(12) United States Patent
Baker et al.

(10) Patent No.: US 9,267,134 B2
(45) Date of Patent: Feb. 23, 2016

(54) METHODS OF MODULATING MICRORNAS IN THE TREATMENT OF PULMONARY ARTERIAL HYPERTENSION

(75) Inventors: Andrew Baker, Glasgow (GB); Margaret MacLean, Glasgow (GB); Nicholas Morrell, Cambridge (GB)

(73) Assignees: The University Court of the University of Glasgow, Glasgow (GB); Cambridge Enterprise Limited, Cambridge (GB)

(*) Notice: Subject to any disclaimer, the term of this patent is extended or adjusted under 35 U.S.C. 154(b) by 0 days.

(21) Appl. No.: 14/116,724

(22) PCT Filed: May 9, 2012

(86) PCT No.: PCT/GB2012/051018
§ 371 (c)(1),
(2), (4) Date: Feb. 14, 2014

(87) PCT Pub. No.: WO2012/153135
PCT Pub. Date: Nov. 15, 2012

(65) Prior Publication Data
US 2014/0163086 A1    Jun. 12, 2014

Related U.S. Application Data

(60) Provisional application No. 61/605,376, filed on Mar. 1, 2012, provisional application No. 61/484,091, filed on May 9, 2011.

(51) Int. Cl.
*A61K 48/00* (2006.01)
*C12N 15/113* (2010.01)

(52) U.S. Cl.
CPC ........ *C12N 15/113* (2013.01); *C12N 2310/113* (2013.01); *C12N 2310/14* (2013.01); *C12N 2310/3231* (2013.01)

(58) Field of Classification Search
None
See application file for complete search history.

(56) References Cited

U.S. PATENT DOCUMENTS

2005/0261218 A1* 11/2005 Esau et al. ............... 514/44

FOREIGN PATENT DOCUMENTS

| CN | 101448942 A | 6/2009 |
| CN | 102382824 A | 3/2012 |
| WO | WO 2007/070483 A2 | 6/2007 |
| WO | WO 2009/121031 A1 | 10/2009 |
| WO | WO 2010/104796 A2 | 9/2010 |

OTHER PUBLICATIONS

Cordes et al., "miR-145 and miR-143 regulate smooth muscle cell fate and plasticity," Nature 460:705-711 (2009).
Boettger et al., "Acquisition of the contractile phenotype by murine arterial smooth cells depends on the Mir143/145 gene cluster," J. Clin. Invest. 119(9):2634-2647 (2009).
Courboulin et al., "Role for miR-204 in human pulmonary arterial hypertension," J. Exp. Med. 208(3):535-548 (2011).
International Search Report, PCT Appl. No. PCT/GB2012/051018, 5 pages (Oct. 25, 2012).
Written Opinion of the International Searching Authority, PCT Appl. No. PCT/GB2012/051018, 7 pages (Oct. 25, 2012).
Caruso et al., "Dynamic Changes in Lung MicroRNA Profiles During the Development of Pulmonary Hypertension due to Chronic Hypoxia and Monocrotaline," Arterioscler. Thromb. Vasc. Biol. 30(4):716-723 (2010).

* cited by examiner

*Primary Examiner* — Kimberly Chong
(74) *Attorney, Agent, or Firm* — Cooley LLP

(57) ABSTRACT

The present invention provides a method of treating or preventing pulmonary arterial hypertension in a subject in need thereof by administering to the subject an inhibitor of miR-145 expression or activity. Pharmaceutical compositions and kits comprising miR-145 inhibitors for treating pulmonary arterial hypertension are also disclosed.

20 Claims, 25 Drawing Sheets

A

B

A

B  KLF5 in normoxic conditions

C  KLF4 in normoxic conditions

A

B

METHODS OF MODULATING MICRORNAS IN THE TREATMENT OF PULMONARY ARTERIAL HYPERTENSION

RELATED APPLICATIONS

This application is a U.S. national stage of International Application No. PCT/GB2012/051018, filed May 9, 2012, which claims the benefit of U.S. Provisional Application No. 61/605,376, filed Mar. 1, 2012 and U.S. Provisional Application No. 61/484,091, filed May 9, 2011, each of which is incorporated by reference in its entirety.

FIELD OF THE INVENTION

The present invention relates to the treatment and prevention of pulmonary arterial hypertension by administering agents that modulate the activity or expression of a microRNA (miRNA). In particular, the invention provides a method for treating or preventing pulmonary arterial hypertension by inhibiting the expression or activity of miR-145 in cells of a subject in need thereof.

BACKGROUND OF THE INVENTION

Pulmonary arterial hypertension (PAH) is a disease of the small pulmonary arteries (PAs), characterized by an increase in PA pressure and vascular remodeling leading to a progressive increase in pulmonary vascular resistance (Rich et al., 1987). The consequence of vascular obliteration is right heart failure and high mortality (Jeffery et al., 2002; Voelkel et al., 1997). Germline mutations in the gene coding for the bone morphogenetic protein (BMP) type-2 receptor (BMPR2), a receptor for the transforming growth factor (TGF)-β superfamily, have been identified in approximately 70% of patients with the heritable form of PAH (hPAH) (Morrell et al., 2001). Moreover, BMPR2 expression is also markedly reduced in PAH cases in the absence of mutations in this gene (idiopathic PAH, iPAH), suggesting a broader role for this receptor pathway in the development of PAH. In pulmonary artery smooth muscle cells (PASMCs) mutations in BMPR2 are associated with an abnormal growth response to BMPs and TGF-β. In endothelial cells, these mutations increase the susceptibility of cells to apoptosis (PAECs) (Morrell et al., 2001). The absence of BMPR2 mutations in some families and in the majority of iPAH cases suggests that further pathological mechanisms, possibly related to the TGF-β super-family, still need to be identified.

One of the main histopathological features common to all forms of PAH is the accumulation of cells expressing smooth muscle specific α-actin (SMA) in peripheral pulmonary arteries. This includes the appearance of SMA-positive cells in the neointima and the extension of SMA-positive cells into pre-capillary pulmonary arterioles that are normally devoid of smooth muscle (Mandegar et al., 2004). The cellular processes responsible for the muscularization of this distal part of the PA are not clear, but these observations suggest a central role for PASMCs in the development of PAH.

MicroRNAs (miRNAs) are a class of small, endogenous and non-coding RNAs able to negatively regulate gene expression by targeting specific messenger RNAs (mRNAs) and inducing their degradation or translational repression (Ambros, 2004; Bartel, 2009). A recent study has defined mRNA degradation as the predominant mechanistic effect of miRNA:mRNA targets (Guo et al., 2010). Several recent studies have assessed the direct role of miRNAs in vascular inflammation and in the development of vascular pathologies (Kartha and Subramanian, 2010; Urbich et al., 2008). In a recent study, miR-145 was shown to be abundantly expressed in the vessel wall (Cheng et al., 2009). MiR-145 is transcribed as a long pri-miRNA encoding both miR-143 and miR-145 on human chromosome 5 (Lio et al., 2010) and on mouse chromosome 18, regulated by a conserved SRF-binding site (Xin et al., 2009). Localization of miR-145 to the vessel wall demonstrated high expression in the smooth muscle layer in comparison with adventitial fibroblasts and endothelial cells (Cheng et al., 2009). For this reason, miR-145 is considered a smooth muscle cell phenotypic marker and modulator, able to regulate smooth muscle cell (SMC) maturation and proliferation, and vascular neointimal lesion formation through its target gene KLF-5 and its downstream signaling molecule, myocardin (Cheng et al., 2009; Elia et al., 2009). Agonists within the TGF-β superfamily have been shown to active miR-143/145 cluster via a Smad-dependent pathway (Davis-Dusenbery et al., 2011; Long et al., 2011). Moreover the analysis of miR-145, miR-143 and miR-143/145 knock-out (ko, −/−) mice showed a noticeably thinner smooth muscle layer of the aorta and other peripheral arteries, due to a reduced SMC size induced by a disruption of actin filaments Elia et al., 2009. This leads to moderate systemic hypotension and the absence of neointima formation in response to injury in miR-145 −/− mice (Xin et al., 2009). Moreover, vascular smooth muscle cells (VSMCs) isolated from single and double ko animals showed hyperproliferative activity and a higher ability to migrate towards platelet-derived growth factor (PDGF), a known chemoattractant for VSMCs (Elia et al., 2009; Xin et al., 2009). Furthermore, a pharmacological analysis of the vasculature of miR-143(145) ko mice revealed a blunted response to vasopressive stimuli (Elia et al., 2009; Xin et al., 2009). Taking together, these findings show a dedifferentiated phenotype of VSMCs in miR-145 ko and miR-143/145 double ko mice.

Despite an improved understanding of the underlying genetics, PAH remains a severe and often fatal disease. Extensive remodeling of small pulmonary arteries, including proliferation of pulmonary artery smooth muscle cells (PASMCs), characterizes the pathology. Current treatments for PAH fail to adequately address smooth muscle proliferation that underlies PAH pathology. Thus, there is a need in the art for the development of novel therapies for PAH. MicroRNAs, which have been reported to play a role in vascular remodeling, represent a potential novel therapeutic target the development of effective treatments for PAH.

SUMMARY OF THE INVENTION

The present invention is based, in part, on the discovery that miR-145 is dysregulated in mouse models of PAH and up-regulated in lung tissue of humans suffering from both idiopathic and heritable forms of PAH. Elimination of miR-145 expression in developmental knockout animals confers protection against the development of PAH. Accordingly, the present invention provides a method of treating or preventing PAH in a subject in need thereof by administering to the subject an inhibitor of miR-145 expression or function.

In one embodiment, the method comprises administering to the subject an antisense oligonucleotide that comprises a sequence that is at least partially complementary to a miR-145 sequence (e.g. pri-miR-145, pre-miR-145, or mature miR-145). In certain embodiments, the antisense oligonucleotide comprises a sequence that is at least partially complementary to a human mature miR-145 sequence. The antisense oligonucleotide can contain one or more backbone or sugar modifications, such as phosphorothioate linkages, 2'-O-alkyl modifications, and bicyclic sugar nucleoside modifications (e.g., locked nucleic acids (LNAs)). In some embodiments, the antisense oligonucleotide inhibitors targeting miR-145 are from about 8 to about 18 nucleotides in length. In particular embodiments, the antisense oligonucleotides targeting miR-145 range from about 12 to about 16 nucleotides in length or from about 10 to about 14 nucleotides in length.

In one embodiment, the antisense oligonucleotide is an antimiR. The antimiR is an antisense oligonucleotide that targets and inhibits miR-145. The antimiR can be an LNA antimiR. In one embodiment, the antimiR targets base 2-17 of mature miR-145. In another embodiment, the antimiR is 16 nucleotides in length. In yet another embodiment, the antimiR is fully phosphorothiolated. The antimiR can fully phosphorothiolated and perfectly complementary to the 5' region of miR-145. The antimiR can also be synthesized as a mixer of LNA and DNA.

In another embodiment of the invention, the miR-145 inhibitor is administered to a subject diagnosed with or at risk of developing pulmonary hypertension or pulmonary arterial hypertension (PAH). Forms of pulmonary hypertension the subject may be diagnosed with or at risk of developing include, but are not limited to, idiopathic PAH, hereditary or familial PAH, and secondary pulmonary hypertension (e.g. hypertension resulting from pulmonary emboli, emphysema, pulmonary fibrosis, and congenital heart disease). In one embodiment, the subject is diagnosed with idiopathic PAH or hereditary PAH. In some embodiments, the subject at risk of developing PAH has a mutation in the gene encoding the bone morphogenetic protein type-2 receptor. In a particular embodiment, the subject is human.

The miR-145 inhibitor can be administered to the subject via various routes including, intravenously, intraarterially, nasally, orally, or via a pulmonary route (e.g. via inhalation through the nose or mouth). In certain embodiments, the miR-145 inhibitor is administered by an inhalational route through a pulmonary delivery device. In such embodiments, the miR-145 inhibitor may be formulated as a dry powder or liquid aerosol.

The present invention also includes a kit for the treatment or prevention of pulmonary arterial hypertension. In one embodiment, the kit comprises an inhibitor of miR-145 as described herein and an administration device. The administration device can be designed for pulmonary delivery, such as inhalers, nebulizers, insufflators, droppers, and aerosolizers. In other embodiments, the administration device can be designed for intravenous or intraarterial delivery, such as a catheter. The miR-145 inhibitor may be optionally formulated to be stored in the administration device. The kit may further comprise instructions for administering the miR-145 inhibitor to a subject (e.g human) for treating or preventing PAH.

DETAILED DESCRIPTION OF THE INVENTION

Figure 1:
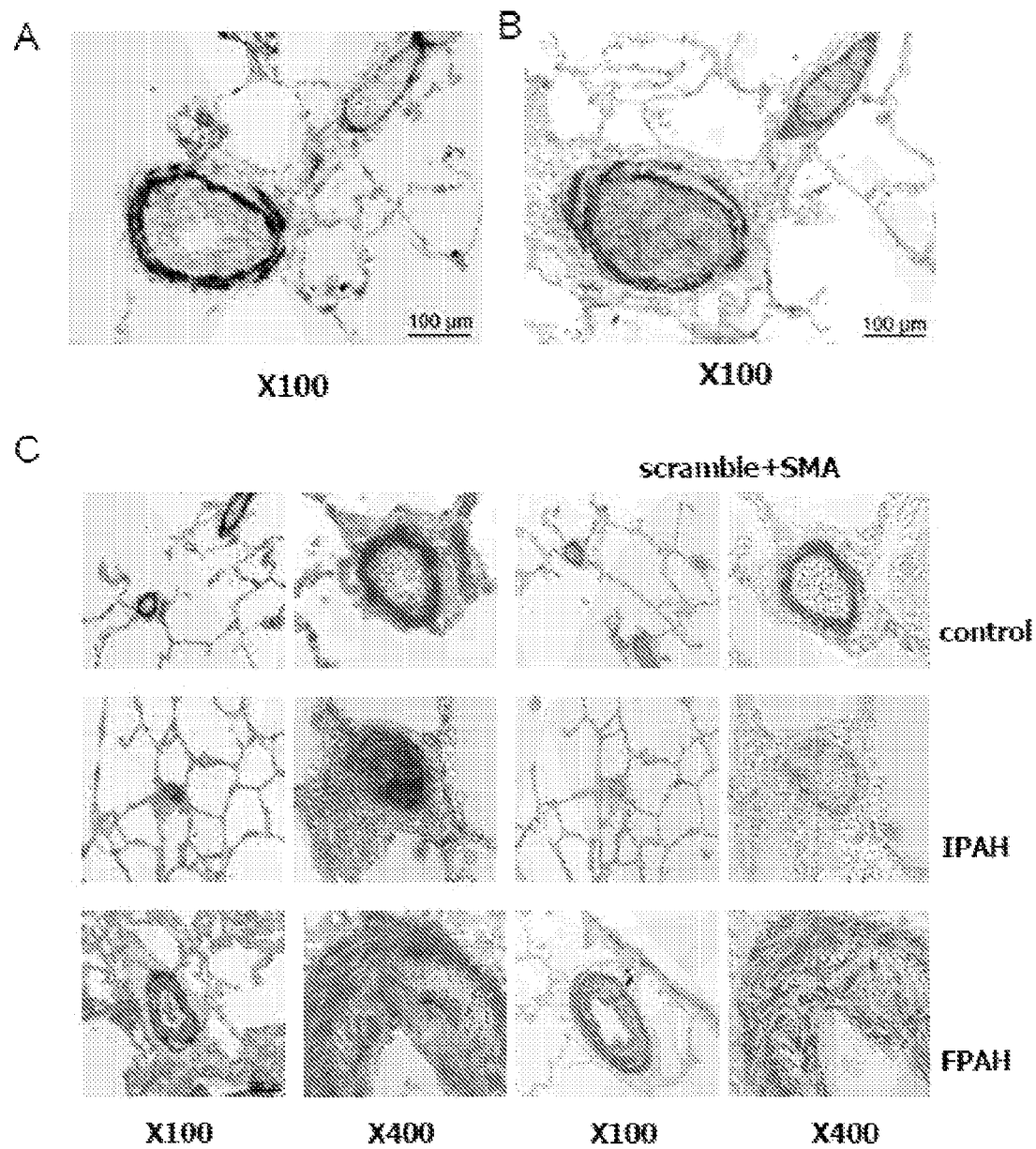
FIG. 1. Co-localization of the miR145 probe to SMC. Normal human lung sections were processed for miR145 and SMA staining as detailed in the Examples. (A) miR145 probe and SM actin, (B) Control probe and SM actin. Mag×10. (C) Analysis in normal human lung and lung from patients with iPAH and fPAH.

The present invention is based, in part, on the surprising discovery that miR-145 expression and function play a critical role in the development of pulmonary arterial hypertension (PAH). The inventors have shown that miR-145 is significantly up-regulated in mice in response to chronic hypoxia and that genetic or pharmacological inhibition of miR-145 is protective against the development of PAH in mice. In human tissues, the inventors report elevation of pre- and mature forms of miR-145 in lung tissues and isolated pulmonary artery smooth muscle cells (PASMCs) obtained from PAH patients with a mutation in the BMPR2 gene compared to controls. Thus, the present invention provides miR-145 as a new target for therapeutic intervention for PAH.

In one embodiment, the present invention provides a method of treating or preventing pulmonary hypertension, particularly PAH, in a subject in need thereof comprising administering to the subject an inhibitor of miR-145 expression and/or activity. Pulmonary hypertension results when pulmonary arteries in the lungs become narrowed, blocked, or damaged causing an increase in arterial pressure. The enhanced workload on the right ventricle causes strain on the heart muscle and can lead to heart failure. Symptoms of PAH include, but are not limited to, shortness of breath, initially while exercising and eventually while at rest, fatigue, dizziness or fainting spells, chest pressure or pain, swelling in lower extremities (ankles and legs) and abdomen, bluish color to skin and lips, and racing pulse or heart palpitations. Preferably, one or more of the aforesaid symptoms is improved or eliminated, or development of PAH is retarded, in a subject suffering from PAH following administration of the miR-145 inhibitor as compared to a subject not receiving treatment. In some embodiments, the right ventricular systolic pressure in the subject is reduced following administration of the miR-145 inhibitor.

Forms of pulmonary hypertension that can be treated with the methods of the invention include, but are not limited to, idiopathic PAH, hereditary or familial PAH, and secondary pulmonary hypertension (e.g. hypertension resulting from pulmonary emboli, emphysema, pulmonary fibrosis, and congenital heart disease). Familial or hereditary forms of PAH have been linked to mutations in certain genes. For instance, 70% of patients with the heritable form of PAH have mutations in the gene encoding bone morphogenetic protein (BMP) type-2 receptor (BMPR2) (Morrell et al., 2001). Thus, in some embodiments, the subject to be treated with the methods of the invention is at risk for developing PAH. In one embodiment, the subject (e.g. a human) at risk has a mutation in the gene encoding for BMPR2.

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

MiR-145 is located in a cluster with miR-143 in an intergenic region on murine chromosome 18 and human chromosome 5. MiR-145 and miR-143, which have no homology to each other, are co-transcribed as a single transcript. The pre-miRNA sequence for miR-145 is processed into a mature sequence and a star (i.e. minor) sequence. The star sequence is processed from the other arm of the stem loop structure. The pre-miRNA (e.g. stem-loop sequences), mature, and star sequences for mouse and human miR-145 are given below:

```
Human mature miR-145
                                                (SEQ ID NO: 1)
5'-GUCCAGUUUUCCCAGGAAUCCCU-3'

Human miR-145*
                                                (SEQ ID NO: 2)
5'-GGAUUCCUGGAAAUACUGUUCU-3'

Human pre-miR-145
                                                (SEQ ID NO: 3)
5'-CACCUUGUCCUCACGGUCCAGUUUUCCCAGGAAUCCCUUAGAUGCUA

AGAUGGGGAUUCCUGGAAAUACUGUUCUUGAGGUCAUGGUU-3'

Mouse mature miR-145
                                                (SEQ ID NO: 4)
5'-GUCCAGUUUUCCCAGGAAUCCCU-3'

Mouse miR-145*
                                                (SEQ ID NO: 5)
5'-AUUCCUGGAAAUACUGUUCUUG-3'

Mouse pre-miR-145
                                                (SEQ ID NO: 6)
5'-CUCACGGUCCAGUUUUCCCAGGAAUCCCUUGGAUGCUAAGAUGGGGA

UUCCUGGAAAUACUGUUCUUGAG-3'
```

The above sequences can be either ribonucleic acid sequences or deoxyribonucleic acid sequences or a combination of the two (i.e. a nucleic acid comprising both ribonucleotides and deoxyribonucelotides). It is understood that a nucleic acid comprising any one of the sequences described herein will have a thymidine base in place of the uridine base for DNA sequences and a uridine base in place of a thymidine base for RNA sequences.

Inhibitors of miR-145 expression or activity suitable for use in methods of the invention include antisense oligonucleotides, antagomirs, synthetic ribozymes, or aptamers. In certain embodiments, an inhibitor of miR-145 is an antisense oligonucleotide. The antisense oligonucleotides can include ribonucleotides or deoxyribonucleotides or a combination thereof. Preferably, the antisense oligonucleotides have at least one chemical modification (e.g., sugar or backbone modification). For instance, suitable antisense oligonucleotides can be comprised of one or more "conformationally constrained" or bicyclic sugar nucleoside modifications (BSN) that confer enhanced thermal stability to complexes formed between the oligonucleotide containing BSN and their complementary microRNA target strand. For example, in one embodiment, the antisense oligonucleotides contain at least one "locked nucleic acid." Locked nucleic acids (LNAs) contain the 2'-O, 4'-C-methylene ribonucleoside (structure A) wherein the ribose sugar moiety is in a "locked" conformation. In another embodiment, the antisense oligonucleotides contain at least one 2',4'-C-bridged 2' deoxyribonucleoside (CDNA, structure B). See, e.g., U.S. Pat. No. 6,403,566 and Wang et al. (1999) Bioorganic and Medicinal Chemistry Letters, Vol. 9: 1147-1150, both of which are herein incorporated by reference in their entireties. In yet another embodiment, the antisense oligonucleotides contain at least one modified nucleoside having the structure shown in structure C. The antisense oligonucleotides targeting miR-145 can contain combinations of BSN (LNA, CDNA and the like) or other modified nucleotides, and ribonucleotides or deoxyribonucleotides. In some embodiments, the antisense oligonucleotides targeting miR-145 comprise a combination of LNA and DNA nucleotides.

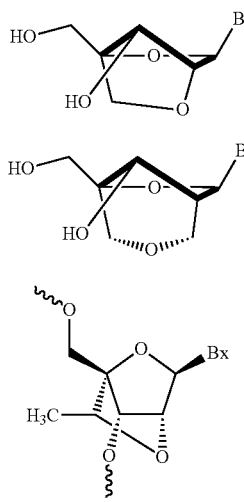

Alternatively, the antisense oligonucleotides can comprise peptide nucleic acids (PNAs), which contain a peptide-based backbone rather than a sugar-phosphate backbone. Other modified sugar or phosphodiester modifications to the antisense oligonucleotide are also contemplated. For instance, other chemical modifications that the antisense oligonucleotides can contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In certain embodiments, the antisense oligonucleotide comprises a full phosphorothioate-linked backbone. In one embodiment, antisense oligonucleotides targeting miR-145 contain 2'O-methyl sugar modifications on each base and are linked by phosphorothioate linkages. Antisense oligonucleotides, particularly those of shorter lengths (e.g., less than 15 nucleotides) can comprise one or more affinity enhancing modifications, such as, but not limited to, LNAs, bicyclic nucleosides, phosphonoformates, 2' O-alkyl modifications and the like. In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. For instance, to facilitate in vivo delivery and stability, the antisense oligonucleotide can be linked to a steroid, such as cholesterol moiety, a vitamin, a fatty acid, a carbohydrate or glycoside, a peptide, or other small molecule ligand at its 3' end.

Preferable antisense oligonucleotides useful for inhibiting the activity of miRNAs are about 5 to about 25 nucleotides in length, about 10 to about 30 nucleotides in length, or about 20 to about 25 nucleotides in length. In certain embodiments, antisense oligonucleotides targeting miR-145 are about 8 to about 18 nucleotides in length, about 12 to about 16 nucleotides in length, about 10 to about 14 nucleotides in length, or about 11 to about 15 nucleotides in length. Any 8-mer or longer complementary to miR-145 may be used.

For instance, in one embodiment, the antisense oligonucleotide has a sequence of 5'-AGGGAUUCCUGG-GAAAACUGGAC-3' (SEQ ID NO: 7). In another embodiment, the antisense oligonucleotide has a sequence of 5'-CCUGGGAAAACUGGAC-3' (SEQ ID NO: 8). In another embodiment, the antisense oligonucleotide has a sequence of 5'-UGGGAAAACUGGAC-3' (SEQ ID NO: 9). In another embodiment, the antisense oligonucleotide has a sequence of 5'-GGAAAACUGGAC-3' (SEQ ID NO: 10). In yet another embodiment, the antisense oligonucleotide has a sequence of 5'-AAAACUGGAC-3' (SEQ ID NO: 11). In still another embodiment, the antisense oligonucleotide has a sequence of 5'-AACUGGAC-3' (SEQ ID NO: 12). Antisense oligonucleotides can comprise a sequence that is at least partially complementary to a mature or minor (i.e. star) miR-145 sequence, e.g. at least about 75%, 80%, 85%, 90%, 95%, 96%, 97%, 98%, or 99% complementary to a mature or minor (i.e. star) miR-145 sequence (e.g., SEQ ID NO: 1 or SEQ ID NO: 2). In some embodiments, the antisense oligonucleotide can be substantially complementary to a mature or minor miR-145 sequence, that is at least about 90%, 95%, 96%, 97%, 98%, or 99% complementary to a target polynucleotide sequence. In one embodiment, the antisense oligonucleotide comprises a sequence that is 100% complementary to a mature or minor miR-145 sequence. In certain embodiments, the antisense oligonucleotide is at least partially complementary to SEQ ID NO: 1. In other embodiments, the antisense oligonucleotide is at least partially complementary to SEQ ID NO: 2.

The antisense can be an antimiR, an antisense oligonucleotide that is partially or fully complementary to a miR. The antimiR can be complementary to the 5' end of the miRNA and progressing across the full complementary sequence of the miRNA, such as comprising or having a sequence of SEQ ID NOs: 7-12. The antimiR can comprise a sequence that is at least partially complementary to a mature or minor (i.e. star) miR-145 sequence, e.g. at least about 75%, 80%, 85%, 90%, 95%, 96%, 97%, 98%, or 99% complementary to a mature or minor (i.e. star) miR-145 sequence (e.g., SEQ ID NO: 1 or SEQ ID NO: 2). In some embodiments, the antimiR can be substantially complementary to a mature or minor miR-145 sequence, that is at least about 90%, 95%, 96%, 97%, 98%, or 99% complementary to a target polynucleotide sequence. In one embodiment, the a antimiR comprises a sequence that is 100% complementary to a mature or minor miR-145 sequence. In certain embodiments, the antimiR is at least partially complementary to SEQ ID NO: 1. In other embodiments, the antimiR is at least partially complementary to SEQ ID NO: 2.

The antimiR can be about 5 to about 25 nucleotides in length, about 10 to about 30 nucleotides in length, or about 20 to about 25 nucleotides in length. In certain embodiments, an antimiR targeting miR-145 is about 8 to about 18 nucleotides in length, about 12 to about 16 nucleotides in length, about 10 to about 14 nucleotides in length, or about 11 to about 15 nucleotides in length. In one embodiment, the antimiR is about 16 nucleotides in length. The antimiR can be fully, partially, or not phosphorothiolated. In one embodiment, the antimiR is a LNA antimiR. In one embodiment, the antimiR targets base 2-17 of mature miR-145. For example, the antimiR can have the sequence of 5'-UCCUGG-GAAAACUGGA-3' (SEQ ID NO: 13). In one embodiment, the antimiR has the sequence of SEQ ID NO: 13 and is fully phosphorothiolated. In yet another embodiment, the antimiR having the sequence of SEQ ID NO: 13 is a LNA antimiR.

The antimiR having the sequence of SEQ ID NO: 13 can be a mixture of LNA and DNA. In yet another embodiment, the antimiR having the sequence of SEQ ID NO: 13 is a LNA antimiR that is fully phosphorothiolated.

In some embodiments, the antisense oligonucleotides are antagomirs. "Antagomirs" are single-stranded, chemically-modified ribonucleotides that are at least partially complementary to a miR-145 sequence. Antagomirs may comprise one or more modified nucleotides, such as 2'-O-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting miR-145 can be about 15 to about 50 nucleotides in length, about 18 to about 30 nucleotides in length, about 20 to about 25 nucleotides in length, or about 10 to about 14 nucleotides in length. The antagomirs can be at least about 75%, 80%, 85%, 90%, 95%, 96%, 97%, 98%, or 99% complementary to a mature or minor miR-145 sequence. In some embodiments, the antagomir may be substantially complementary to a mature or minor miR-145 sequence, that is at least about 95%, 96%, 97%, 98%, or 99% complementary to a target polynucleotide sequence. In other embodiments, the antagomirs are 100% complementary to a mature or minor miR-145 sequence.

The inhibitory nucleotide molecules described herein preferably target the mature sequence of miR-145 (SEQ ID NO: 1). In one embodiment, the inhibitory nucleotide molecules described herein target the minor (i.e. star) sequence of miR-145 (SEQ ID NO: 2). In some embodiments, inhibitors of miR-145 are antagomirs comprising a sequence that is perfectly complementary to the mature or minor miR-145 sequence. In one embodiment, an inhibitor of miR-145 is an antagomir having a sequence that is partially or perfectly complementary to SEQ ID NO: 1. In another embodiment, an inhibitor of miR-145 is an antagomir having a sequence that is partially or perfectly complementary to SEQ ID NO: 2. In some embodiments, inhibitors of miR-145 are chemically-modified antisense oligonucleotides. In one embodiment, an inhibitor of miR-145 is a chemically-modified antisense oligonucleotide comprising a sequence substantially complementary to SEQ ID NO: 1. In another embodiment, an inhibitor of miR-145 is a chemically-modified antisense oligonucleotide comprising a sequence substantially complementary to SEQ ID NO: 2. As used herein "substantially complementary" refers to a sequence that is at least about 95%, 96%, 97%, 98%, 99%, or 100% complementary to a target polynucleotide sequence (e.g. mature, minor, or precursor miRNA sequence).

Antisense oligonucleotides or antagomirs may comprise a sequence that is substantially complementary to a precursor miRNA sequence (pre-miRNA) or primary miRNA sequence (pri-miRNA) for miR-145. In some embodiments, the antisense oligonucleotide comprises a sequence that is substantially complementary to a sequence located outside the stem-loop region of the pre-miR-145 sequence. In one embodiment, an inhibitor of miR-145 function is an antisense oligonucleotide having a sequence that is substantially complementary to a pre-miR-145 sequence (SEQ ID NO: 3).

Any of the inhibitors of miR-145 described herein can be delivered to the target cell (e.g. smooth muscle cell) by delivering to the cell an expression vector encoding the miR-145 inhibitors. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing an inhibitor of miR-145 comprises a promoter operably linked to a polynucleotide encoding an antisense oligonucleotide, wherein the sequence of the expressed antisense oligonucleotide is partially or perfectly complementary to a mature or minor sequence of miR-145 (e.g., SEQ ID NO: 1 or SEQ ID NO: 2). The phrase "operably linked" or "under transcriptional control" as used herein means that the promoter is in the correct location and orientation in relation to a polynucleotide to control the initiation of transcription by RNA polymerase and expression of the polynucleotide.

As used herein, a "promoter" refers to a DNA sequence recognized by the synthetic machinery of the cell, or introduced synthetic machinery, required to initiate the specific transcription of a gene. Suitable promoters include, but are not limited to RNA pol I, pol II, pol III, and viral promoters (e.g. human cytomegalovirus (CMV) immediate early gene promoter, the SV40 early promoter, and the Rous sarcoma virus long terminal repeat). In one embodiment, the promoter is a tissue-specific promoter. Of particular interest are vascular specific promoters, and more particularly, smooth muscle specific promoters, such as alpha smooth muscle actin promoter. Other suitable promoters include the myosin light chain-2 promoter (Franz et al. (1994) *Cardioscience*, Vol. 5(4):235-43; Kelly et al. (1995) *J. Cell Biol.*, Vol. 129(2):383-396), the alpha actin promoter (Moss et al. (1996) *Biol. Chem.*, Vol. 271(49):31688-31694), the troponin 1 promoter (Bhaysar et al. (1996) *Genomics*, Vol. 35(1):11-23); the Na+/Ca2+ exchanger promoter (Barnes et al. (1997) 1 *Biol. Chem.*, Vol. 272(17):11510-11517), the dystrophin promoter (Kimura et al. (1997) *Dev. Growth Differ.*, Vol. 39(3):257-265), the alpha7 integrin promoter (Ziober and Kramer (1996) *J. Bio. Chem.*, Vol. 271(37):22915-22), the brain natriuretic peptide promoter (LaPointe et al. (1996) *Hypertension*, Vol. 27(3 Pt 2):715-22) and the alpha B-crystallin/small heat shock protein promoter (Gopal-Srivastava (1995) *J. Mol. Cell. Biol.*, Vol. 15(12):7081-7090), alpha myosin heavy chain promoter (Yamauchi-Takihara et al. (1989) *Proc. Natl. Acad. Sci. USA*, Vol. 86(10):3504-3508) and the ANF promoter (LaPointe et al. (1988) *J. Biol. Chem.*, Vol. 263(19): 9075-9078).

In certain embodiments, the promoter operably linked to a polynucleotide encoding a miR-145 inhibitor can be an inducible promoter. Inducible promoters are known in the art and include, but are not limited to, tetracycline promoter, metallothionein IIA promoter, heat shock promoter, steroid/thyroid hormone/retinoic acid response elements, the adenovirus late promoter, and the inducible mouse mammary tumor virus LTR.

Methods of delivering expression constructs and nucleic acids to cells are known in the art and can include, for example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

The present invention also includes methods for scavenging or clearing miR-145 inhibitors following treatment. The method may comprise overexpressing binding sites for the miR-145 inhibitors in lung tissue. The binding site regions preferably contain a sequence of the seed region for miR-145. The seed region is the 5' portion of a miRNA spanning bases 2-8, which is important for target recognition. In some embodiments, the binding site may contain a sequence from the 3'UTR of one or more targets of miR-145, such as KLF4, KLF-5, Srgap1, and Srgap2.

The present invention also includes pharmaceutical compositions comprising an inhibitor of miR-145. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

In one embodiment, the pharmaceutical composition comprises an effective dose of a miR-145 inhibitor and a pharmaceutically acceptable carrier. For instance, the pharmaceutical composition comprises and effective dose of a modified antisense oligonucleotide targeting miR-145 as described herein. In some embodiments, the pharmaceutical composition comprises a modified antisense oligonucleotide having a sequence selected from the group consisting of SEQ ID NO: 7, SEQ ID NO: 8, SEQ ID NO: 9, SEQ ID NO: 10, SEQ ID NO: 11, and. In one embodiment, the pharmaceutical composition comprises an effective dose of a synthetic antisense oligonucleotide, such as an antimiR having the sequence of SEQ ID NO: 13. In one embodiment, the pharmaceutical composition comprises an effective dose of an antimiR having SEQ ID NO: 13, that is fully phosphorothiolated. In yet another embodiment, the pharmaceutical composition comprises an effective dose of a LNA antimiR having SEQ ID NO: 13, wherein the antimiR is fully phosphorothiolated.

An "effective dose" is an amount sufficient to effect a beneficial or desired clinical result. An effective dose of a miRNA inhibitor of the invention may be from about 0.001 mg/kg to about 100 mg/kg, about 0.01 mg/kg to about 10 mg/kg, about 0.1 mg/kg to about 10 mg/kg, about 1 mg/kg to about 10 mg/kg, about 2.5 mg/kg to about 50 mg/kg, or about 5 mg/kg to about 25 mg/kg. The precise determination of what would be considered an effective dose may be based on factors individual to each patient, including their size, age, type and severity of pulmonary arterial hypertension, and nature of inhibitor (e.g. antagomir, expression construct, antisense oligonucleotide, etc). Therefore, dosages can be readily ascertained by those of ordinary skill in the art from this disclosure and the knowledge in the art.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of miR-145 function or constructs expressing particular miRNA inhibitors. In certain embodiments, the miR-145 inhibitors are formulated for pulmonary delivery. As used herein "pulmonary delivery" or "respiratory delivery" refer to delivery of miR-145 inhibitors to a subject by inhalation through the mouth or nose and into the lungs. For example, the miR-145 inhibitors can be formulated as a snuff, aerosol, solution for a nebulizer, or as a microfine powder for insufflation. In embodiments in which the miR-145 inhibitor is formulated as a dry powder, the particles of active compound suitably have diameters of less than 50 microns, preferably less than 10 microns, such as between 1 and 5 microns or between 2 and 5 microns.

One will generally desire to employ appropriate salts and buffers to render delivery vehicles stable and allow for uptake by target cells. Aqueous compositions of the present invention comprise an effective amount of the delivery vehicle comprising the inhibitor polynucleotides (e.g. liposomes or other complexes or expression vectors) dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal, intraarterial, or intravenous injection. In certain embodiments, pharmaceutical compositions comprising miR-145 inhibits are administered by inhalation. Pharmaceutical compositions comprising miRNA inhibitors or expression constructs comprising miRNA inhibitors may also be administered by catheter systems or systems that isolate coronary/pulmonary circulation for delivering therapeutic agents to the heart and lungs. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use, catheter delivery, or inhalational delivery include, for example, sterile aqueous solutions or dispersions and sterile powders for the extemporaneous preparation of sterile injectable solutions or dispersions (e.g. aerosols, nebulizer solutions). Generally, these preparations are sterile and fluid to the extent that easy injectability or aerosolization/nebulization exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof. In some embodiments, sterile powders can be administered directly to the subject (i.e. without reconstitution in a diluent), for example, through an insufflator or inhalation device.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids), or from organic acids (e.g., acetic, oxalic, tartaric, mandelic, and the like). Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules, unit dose inhalers, and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous, intraarterial, and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In another embodiment of the present invention, an inhibitor of miR-145 is used in combination with other therapeutic modalities, for instance, other agents that inhibit PAH. Examples of combination therapies include any of the foregoing. Combinations may be achieved with a single composition or pharmacological formulation that includes both agents, or with two distinct compositions or formulations, at the same time, wherein one composition includes the miR-145 inhibitor and one more other agents. Alternatively, the therapy using a miR-145 inhibitor may precede or follow administration of the other agent(s) by intervals ranging from minutes to weeks. In embodiments where the other agent and miR-145 inhibitor are applied separately to the cell, one would generally ensure that a significant period of time did not expire between the time of each delivery, such that the agent and the miR-145 inhibitor would still be able to exert an advantageously combined effect on the cell. In such instances, it is contemplated that one would typically contact the cell with both modalities within about 12-24 hours of each other, within about 6-12 hours of each other, or with a delay time of only about 12 hours. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In one embodiment, more than one administration of the miR-145 inhibitor or the other agent(s) will be desired. In this regard, various combinations may be employed. By way of illustration, where the miR-145 inhibitor is "A" and the other agent is "B," the following permutations based on 3 and 4 total administrations are provided as examples: A/B/A, B/A/B, B/B/A, A/A/B, B/A/A, A/B/B, B/B/B/A, B/B/A/B, A/A/B/B, A/B/A/B, A/B/B/A, B/B/A/A, B/A/B/A, B/A/A/B, B/B/B/A, A/A/A/B, B/A/A/A, A/B/A/A, A/A/B/A, A/B/B/B, B/A/B/B, B/B/A/B. Other combinations are likewise contemplated. Specific examples of other agents and therapies are provided below.

In one embodiment of the present invention, the method of inhibiting, preventing, or treating PAH in a subject in need thereof comprises administering to the subject a miR-145 inhibitor, such as an antimiR-145 as described herein, and a second agent that inhibits, prevents or treats PAH, and one or more additional agent(s). In one embodiment, a combination of different miR-145 inhibitors are administered, such as an antimiR-145 as described herein, and a small molecule inhibitor of miR-145.

In one embodiment, the additional or other agent is an agonist of miR-204. The human miR-204-5p sequence is 5'-UUCCCUUUGUCAUCCUAUGCCU-3' (SEQ ID NO: 15). The human miR-204-3p sequence is 5'-GCUGGGAAG-GCAAAGGGACGU-3' (SEQ ID NO: 16). An agonist of miR-204 can be a polynucleotide comprising a mature miR-204 sequence. In some embodiments, the polynucleotide comprises the sequence of the pri-miRNA or pre-miRNA sequence for miR-204. The polynucleotide comprising the mature miR-204, pre-miR-204, or pri-miR-204 sequence can be single stranded or double stranded. In one embodiment, the miR-204 agonist can be about 15 to about 50 nucleotides in length, about 18 to about 30 nucleotides in length, about 20 to about 25 nucleotides in length, or about 10 to about 14 nucleotides in length. The miR-204 agonist can be at least about 75%, 80%, 85%, 90%, 95%, 96%, 97%, 98%, 99%, or 100% identical to the mature, pri-miRNA or pre-miRNA sequence of miR-204. In one embodiment, the miR-204 agonist has the sequence of SEQ ID NO: 15 or 16. The miR204 agonist that is a polynucleotide can contain one or more chemical modifications, such as locked nucleic acids, peptide nucleic acids, sugar modifications, such as 2'-O-alkyl (e.g. 2'-O-methyl, 2'-0-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-204 sequence is conjugated to cholesterol. The polynucleotide comprising a miR-204 sequence can be expressed in vivo from a vector and/or operably linked to a promoter, such as described above.

In another embodiment, the agonist of miR-204 can be an agent distinct from miR-204 that acts to increase, supplement, or replace the function of miR-204. For instance, agents that inhibit PDGF, endothelin-1, angiotensin II, and STAT3 expression or activity can be used in combination with a miR-145 inhibitor for treating, preventing or preventing PAH. The agent may be delivered in the form of a polypeptide, peptide, small organic molecule, nucleic acid encoding a polypeptide of interest, and the like. A polypeptide may be any translation product of a nucleic acid regardless of size and glycosylation. An agent may also be in the form of a simple drug, peptide, peptide fragment, DNA, RNA, ribozyme or engineered hybrid of a nucleic acid and peptide or peptide fragment, or a derivative of each.

A combination for treating, preventing or preventing PAH can also comprise a miR-145 inhibitor and a blood vessel dilator (vasodilator), such as, but not limited to epoprostenol. Other agents that can be used with a miR-145 inhibitor include, but are not limited to, an endothelin receptor antagonist, such as bosentan, sitaxentan, and ambriesentan; phosphodiesterase inhibitor, such as phosphodiesterase type 5 inhibitors, sildenafil and tadalafil; calcium channel blocker, such as amlodipine, diltiazem, and nifedipine; prostaglandin, such as treprostinil, iloprost and beraprost; isosorbide dinitrate; and guanylate cyclase activator, such as cinaciguat and riociguat.

An anticoagulant or compound that blocks or inhibits thrombin can also be used, such as, warfarin and compounds based on the tripeptide motif D-Phe-Pro-Arg; e.g., LY287045, etc. Many compounds, such as inogatran and melagatran, are known in the art and can also be used. For non-limiting examples, see U.S. Pat. Nos. 6,326,386; 6,232,315; 6,201,006; 6,174,855; 6,060,451; and 5,985,833; among others.

Additional agents that can be used with a miR-145 inhibitor include an angiotensin converting enzyme inhibitor; nicotine receptor agonist; agent that increases concentrations of nitric oxide, anti-angiogenic agent; agonist of the TGF-β receptor; and death domain receptor ligand.

Angiotensin converting enzyme inhibitors (ACE-I) that can also be used in combination with a miR-145 inhibitor for treating, preventing or preventing PAH include, but are not limited to, captopril, benazepril, enalapril, fosinopril, lisinopril, quinapril, Ramipril, imidapril, perindopril, erbumine, and trandolapril. ACE receptor blockers may also be used in place of or as well as ACE inhibitors, and these include, but are not limited to, losartan, irbesartan, candesartan, cilexetil, and valsartan.

Nicotine receptor agonists, e.g., nicotine (S-3-(1-methyl-2-pyrrolidinyl)pyridine) and other compounds that substantially specifically bind a nicotine receptor and provide a pharmacological effect can also be used in combination with a miR-145 inhibitor for treating, preventing or preventing PAH. Nicotine receptor agonists encompass naturally-occurring compounds (including, but not limited to, small molecules, polypeptides, peptides, and the like, such as naturally-occurring plant alkaloids), endogenous ligands (e.g., purified from a natural source, recombinantly produced, or synthetic, and further including derivatives and variants of such endogenous ligands), and synthetically produced compounds (e.g., small-molecules, peptides, etc.). The term "nicotine" further includes any pharmacologically acceptable derivative or metabolite of nicotine which: exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof.

A miR-145 inhibitor can also be used with one or more agents that increase nitric oxide for treating, preventing or preventing PAH. Examples of nitric oxide promoting agents include, but are not limited to, S-nitrosopenicillamine, sodium nitroprusside, N-ethyl-2-(1-ethyl-2-hydroxy-2nitrosohydrazino) ethanamine (NOC 12), and others. The production of nitric oxide may also be modulated by cytokines, such as γ-interferon, tumor necrosis factor, IL-1, IL-2 and endotoxin due to their effect on the enzyme, nitric oxide synthase. The inducible form of NO synthase is increased by cytokines and the constitutive form seems to be decreased by cytokines. HMG-CoA reductase inhibitors have been found to upregulate endothelial cell NOS activity, as described by U.S. Pat. No. 6,147,109, Liao et al. Any of the forms of nitric oxide synthase can be utilized, as the protein or an active fragment derived therefrom, or as a DNA construct for expression.

Agents with an anti-angiogenic effect can also be used in combination with a miR-145 inhibitor for treating, preventing or preventing PAH. These include, but are not limited to the anti-angiogenic polypeptides: angiostatin; endostatin; and anti-angiogenic anti-thrombin III; and the like, and further include functionally active variants and derivatives thereof. Other anti-angiogenic agents include inhibitors of matrix metalloproteases, e.g., amifostine, WR-1065; marimastat, primomastat, a-1 antitrypsin; sphingosine and the like.

Agonists of the TGF-β receptor are also of interest. TGF-β receptor Type I and type II mediate most activities of TGF-β. Ligands include TGF-β, and mimetics and biologically active derivatives thereof.

Other agents of interest for use with a miR-145 inhibitor include death domain receptor ligands, which are compounds, usually polypeptide compounds that bind to mammalian cell surface receptors comprising a death domain or homologs or orthologs thereof, and that, by binding so deliver a signal for apoptosis to the cell. The intracellular protein interactions triggered by these receptors can be attributed to binding interactions of the death domain, which is homologous to an approximately 80 amino acid domain near the C-terminus of TNF-R1, and is responsible for signaling cytotoxicity. The TNF receptor death domain family includes TNF-R1, Fas (CD95), TRAMP (wsl/Apo-3/DR-3), TRAIL-R1 (DR-4) and TRAIL-R2 (DR-5, TRICK2, KILLER). Death domain ligands include proteins that regulate cellular proliferation and differentiation by binding to specific death domain receptors. These ligands include the TNF family, e.g., TNF, lymphotoxin, CD30 ligand, 4-1 BB ligand, CD40 ligand, CD27 ligand, and TRAIL (TNF-related apoptosis-inducing ligand), and homologs and analogs thereof.

Analogues of rapamycin, such as tacrolimus (FK-506), sirolimus and everolimus, normally used as immunosuppressants but recently discovered to also inhibit the proliferation of vascular smooth muscle cells, may also be used in combination with a miR-145 inhibitor. Antisense knockdown of c-myc, a protein critical for progression of cell replication, is another approach to inhibit cell proliferation in the artery wall, and can be used in combination with a miR-145 inhibitor.

In one embodiment, covalent or non-covalent attachment of antiplatelet agents is also of interest, including GPIIb/IIIa inhibitors, e.g., RheoPro, which can be used in combination with a miR-145 inhibitor. Treatments or therapies such as oxygen therapy, can also be used in combination with administration of a miR-145 inhibitor.

The present invention also includes kits for treating or preventing pulmonary arterial hypertension. In one embodiment, the kit comprises at least one miR-145 inhibitor as described herein and an administration device. In certain embodiments, the administration device is a device designed to deliver the miR-145 inhibitor to the lungs through the nose or mouth. For instance, suitable administration devices for pulmonary delivery include, but are not limited to, droppers, swabs, aerosolizers, insufflators, nebulizers, inhalers (e.g., aerosol-based metered dose inhalers), dry powder dispersion devices, and other pulmonary delivery devices, including manually activated, gas propelled, sonic-driven, and the like. In some embodiments, the miR-145 inhibitor is formulated as a powder contained within the administration device. In other embodiments, the miR-145 inhibitor is formulated as a liquid aerosol contained within the administration device. In a particular embodiment, the administration device is an inhaler. In embodiments in which the miR-145 inhibitor is to be delivered intravenously or intraarterially, the kit can comprise a catheter or other like appropriate administration device. The kit may further comprise instructions for administering an effective dose of the miR-145 inhibitor to a subject to treat pulmonary hypertension. In some embodiment, the kit comprises one or more additional agents or therapies, such as described above.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1

Primary Culture of Human Pulmonary Artery Smooth Muscle Cells (PASMCs)

PASMCs were explanted from peripheral arteries as previously described (Yang et al., 2005). Smooth muscle cell lines were obtained from 4 patients with PAH known to harbor a mutation in BMPR2. These included: 1 patient with a mutation in the kinase domain of BMPR2 in which arginine is substituted for cysteine at position 347 (C347R); 1 patient with a missense mutation in the cytoplasmic tail of BMPR2, leading to a serine in place of asparagine at position 903 (N903S); 1 patient with a truncating mutation at amino acid position 9 (W9X) and 1 patient with a truncating mutation at amino acid position 899 (R899X). Three further PASMC preparations were obtained from unaffected subjects. Cells were cultured as previously described (Yang et al., 2005).

Example 2

RNA Extraction from Frozen Lungs, PASMCs and Reverse Transcription

Total RNA from tissues and cells was obtained using the miRNeasy kit (Qiagen, Hilden, Germany) following the manufacturer's instructions, treated with the DNAse 1 (amplification grade; Sigma, St. Louis, Mo., USA) in order to eliminate genomic DNA contamination and quantified using a NanoDrop ND-1000 Spectrophotometer (Nano-Drop Technologies, Wilmington, Del., USA). cDNA for miRNA analysis was synthesized from total RNA using stem-loop reverse transcription primers according to the TaqMan MiRNA Assay protocol (Applied Biosystems, Foster City, Calif., USA). Each reaction contained 50 ng of extracted total RNA, 50 nM stem-looped RT primer, 1×RT buffer, 0.25 mM each of dNTPs, 3.33 U/ml Multiscribe reverse transcriptase and 0.25 U/ml RNase inhibitor. The 15 ml reactions were incubated in a 96-well plate for 30 minutes at 16° C., 30 minutes at 42° C., 5 minutes at 85° C. and the n held at 4° C. Total cDNA for premiRNA analysis was obtained from total RNA using the SuperScript II Reverse Transcriptase (Invitrogen, Paisley, UK). Each reaction contained 1 mg of total RNA, 1× SuperScript II buffer, 10 U/ml SuperScript II RT, 0.15 mg/ml of random hexamer primers (Invitrogen, Paisley, UK), 1 U/ml of RNase inhibitor (Promega, Madison, Wis., USA) and 0.25 mM each of dNTPs. Cycling conditions were the following: 10 minutes at 25° C., 30 minutes at 48° C., 5 minutes at 95° C. cDNA was stored at −20° C. GAPDH was selected as housekeeping gene due to its stability across all in vivo groups.

Example 3

MiRNA Extraction from Paraffin-Embedded Human Lungs

Formalin fixed paraffin wax embedded tissues blocks were obtained from the Papworth NHS Foundation Trust Hospital Tissue Bank adhering to LREC and HTA guidelines. Lung samples were used from informed and consenting patients undergoing transplantation at Papworth Hospital for end stage pulmonary hypertension. Tissue was obtained from a range of conditions including hPAH associated with mutant BMPR2 (n=5), iPAH (n=6), and controls (n=6). Controls comprised of tissue taken from lobes of lung clear of tumour from patients undergoing pneumonectomy for lung carcinoma and reported free of tumour by a pathologist. The RecoverAll total RNA Isolation kit (Ambion, Streetsville, Canada) was used to extract total RNA (including miRNA) from Formalin-Fixed, Paraffin-Embedded FFPE) samples. Three 10 mm slices were dewaxed with xylene for 3 minutes at 50° C., washed twice with ethanol, and digested with protease at 50° C. for 15 minutes, then for 15 minutes at 80° C. The lysate was passed through a filter cartridge and DNAse digested, then RNA was eluted in 30 ml of RNAse free water and quantified using the NanoDrop ND-1000 Spectrophotometer.

Example 4

TaqMan q-PCR Analysis of Mature miRNAs and mRNAs

For quantitative PCR (q-PCR), 10 ml reactions were incubated in a 386-well optical plate at 95° C. for 10 minutes, following by 40 cycles of 95° C. for 15 seconds and 60° C. for 1 minute. Results were normalized to U6 or Rnu-48 values for mouse and human miRNAs respectively and to GAPDH for pre-miR-145 expression. The fold change for every miRNA expression was obtained using the 2-D D Ct method (1, 2). The q-PCRs for each miRNA were run in triplicate and results are presented as the mean±standard error of samples.

For all the q-PCR experiments values are expressed as fold change or mean±standard deviation. All data were analyzed using a two-way ANOVA followed by Bonferroni's post-hoc test, one-way ANOVA followed by Bonferroni's post-hoc test or unpaired t-test as appropriate, as described in figure legend. *p<0.05, p<0.005, *p<0.001.

Example 5

Microarray Analysis of Wild-Type (Wt) and miR-145 −/− Pulmonary Arteries

Main branch pulmonary arteries were dissected from 6 mice from each group at 10 weeks of age and stored frozen at −80° C. prior to RNA isolation. RNA quantity and quality were assessed by NanoDrop® Spectrophotometer (Thermo Scientific, Wilmington, Del., USA). RNA integrity was assessed with the Agilent 2100 bioanalyser using the RNA 6000 Nano Kit (Santa Clara, Calif.). The Illumina TotalPrep RNA amplification kit (Ambion) was used to generate biotinylated, amplified RNA, from 500 ng input RNA, for hybridization with the Illumina arrays (Applied biosystems Carlsbad, Calif.). The Illumina mouseWG-6 v2.0 Expression beadchips were hybridized following the manufacturers protocol, scanned with the Illumina BeadArray Reader and read into Illumina GenomeStudio® software (version 1.1.1). For microarray data analysis and validation, quantile normalised and background subtracted intensity values were exported from GenomeStudio® software for data processing and analysis in R, in which rank product statistical analysis was carried out. Adjacent comparisons were carried out between the 4 groups. Probes with a false discovery rate less than 0.05 were considered significant. Taqman gene expression assays (Applied Biosystems, Foster City, Calif., USA) were used for target validation on cDNA derived from the 24 samples used for the microarray (n=18 per group).

Example 6

Northern Blot Analysis

Total RNA was separated on a 15% TBE-Urea gel (Invitrogen, Paisley, UK), transferred to an uncharged nylon membrane, Hybond-NX (Amersham Bioscience UK Ltd, Buckingham, UK) using a trans-blot semi-dry system (Bio-Rad Laboratories, Hemel Hempstead, UK), and UV cross-linked. Pre-hybridization was carried out at 55° C. for 30 minutes with hybridization buffer (50% de-ionized formamide, 5×SSPE, 5×Denhardts solution, 0.1% SDS, and 2 μg of heat-denatured herring sperm DNA). Then 25 pmol of miR-145 or U6 miRCURY LNA™ Detection probe, 5'-Digoxigenin (DIG)-labeled (Exiqon, Denmark), were added over night at the same pre-hybridization temperature. Following hybridization, the membrane was washed for 30 minutes at 50° C. with the low stringency wash solution (invitrogen, Paisley, UK) followed by a 30 minutes wash with the high stringency wash solution (invitrogen, Paisley, UK). After that, the membrane was blocked for 30 minutes in blocking solution (1% Blocking reagent in maleic acid) and incubated for 30 minutes with an anti-DIG antibody (Roche Applied Science, Indianapolis, Ind., USA) 1:5000 at room temperature. The CDP Star Chemiluminescent Substrate (Sigma-Aldrich, Poole, UK) was used to detect the presence of the miRNA of interest on the membrane. miRNA quantification was performed with the Scion Image software: band intensities of the miRNA of interest were established and normalized to the relative U6 signal.

Example 7

Immunohistochemistry

Human and mouse lungs were fixed in 4% paraformaldehyde solution at 40° C. for 18 hours and embedded in paraffin. After deparaffinization with graded concentrations of xylene and ethanol, slides were immersed in 3% H2O2 in phosphate buffered saline (PBS) for 30 minutes at room temperature to block endogenous peroxidase activity. Then, they were incubated with 20% normal goat serum for 30 minutes to reduce nonspecific background staining. The sections were then incubated with mouse monoclonal antibody against α-smooth muscle actin (Dako, Clone 1A4, High Wycombe, UK), in 1% (w/v) bovine serum albumin (BSA) in PBS or isotype matched mouse IgG nonimmune control (Dako, High Wycombe, UK). Sections were then incubated with appropriate biotinylated secondary antibody (Dako, High Wycombe, UK) diluted 1:200 in 1% (w/v) BSA in PBS, and then horseradish peroxidase-labeled Extravidin™ (Sigma, St. Louis, Mo., USA) diluted 1:400 in 1% (w/v) BSA in PBS. Staining was visualized using 3.3 diaminobenzidine and the nuclei were counterstained with Mayer's haematoxylin.

Example 8

In Situ Hybridization for Detected miRNA Localization

For the detection of miR-145 in mouse and human lung, sections were rehydrogated with histoclear nd graded concentrations of ethanol. Slides were then boiled for 10 minutes within 10 mM sodium citrate pH 6.0, cooled to room temperature (RT), incubated with 10 mg/ml proteinase K at 37° C. for 15 minutes and finally fixed in 4% PFA for 10 minutes at room temperature in order to allow antigen retrieval. Following antigen retrieval, slides were incubated with hybridisation buffer (50% formamide, 4×SSC, 2.5×Denhardt's solution, 2.5 mg/ml salmon DNA, 0.6 mg/ml yeast tRNA, 0.025% SDS and 0.1% blocking reagent) at 60° C. for 1 hour followed by a 60° C. overnight incubation with 40 nM miR-145 or scramble mercury LNA™ Detection probe, 5'-DIG labeled (Exiqon, Denmark) in the same buffer. Melting temperatures were 79° C. and 78° C., respectively. Immunodetection was performed by blocking the sections in 1% blocking reagent in PBS and 10% FCS for 1 hour at RT followed by a 4° C. over night incubation with an anti-DIG antibody (Roche Applied Science, Indianapolis, Ind., USA) diluted 1:1000. Slides were then incubated with 0.1M Tris pH 9.0 for 5 minutes. In order to stain miR-145, BM purple solution (Roche Applied Science, Mannheim, Germany) or NBT/BCIP solution (Roche Applied Science, Mannheim, Germany) was added to each human or mouse section respectively and left at room temperature for 3 days.

Example 9

Colocalization of SMA and miR145

MicroRNA in situ hybridisation was performed on routinely fixed paraffin-embedded 6 μm human lung sections, as described above. The slides were deparaffinized with histoclear, and treated with 10 ug/ml proteinase K (Sigma) at 37° C. for 20 minutes, then fixed with 4% paraformaldehyde for 10 minutes. After washing with phosphate buffered saline (PBS), slides were incubated with hybridisation buffer at 60 degree for 1 hr. Then slides were hybridised with 40 nM DIG-labelled miR145 or scramble probe (Exiqon) at 60° C. overnight. After washing and blocking, slides were incubated with anti-DIG AP Fab fragments (Roche) in blocking buffer at 4 degree overnight, and washed with PBST (PBS plus 0.1% Tween 20) and 0.1M Tris-HCL (pH 19.5). miR-145 was visualized with BM purple solution (Roche) for 1-2 days at room temperature until the staining was visible under microscope. After washing with PBS, slides were quenched with 0.3% H2O2 in PBS for 10 min. To block non-specific background, 10% rabbit normal serum was applied on slides for 1 hr, then slides were incubated with monoclonal anti-human alpha smooth muscle actin (DAKO) in 10% normal serum at 4° C. overnight. The slides were visualized with 3,3'-diaminobenzidine as chromogen for 5 minutes. The visualization is shown in FIG. 1.

Example 10

Figure 2:
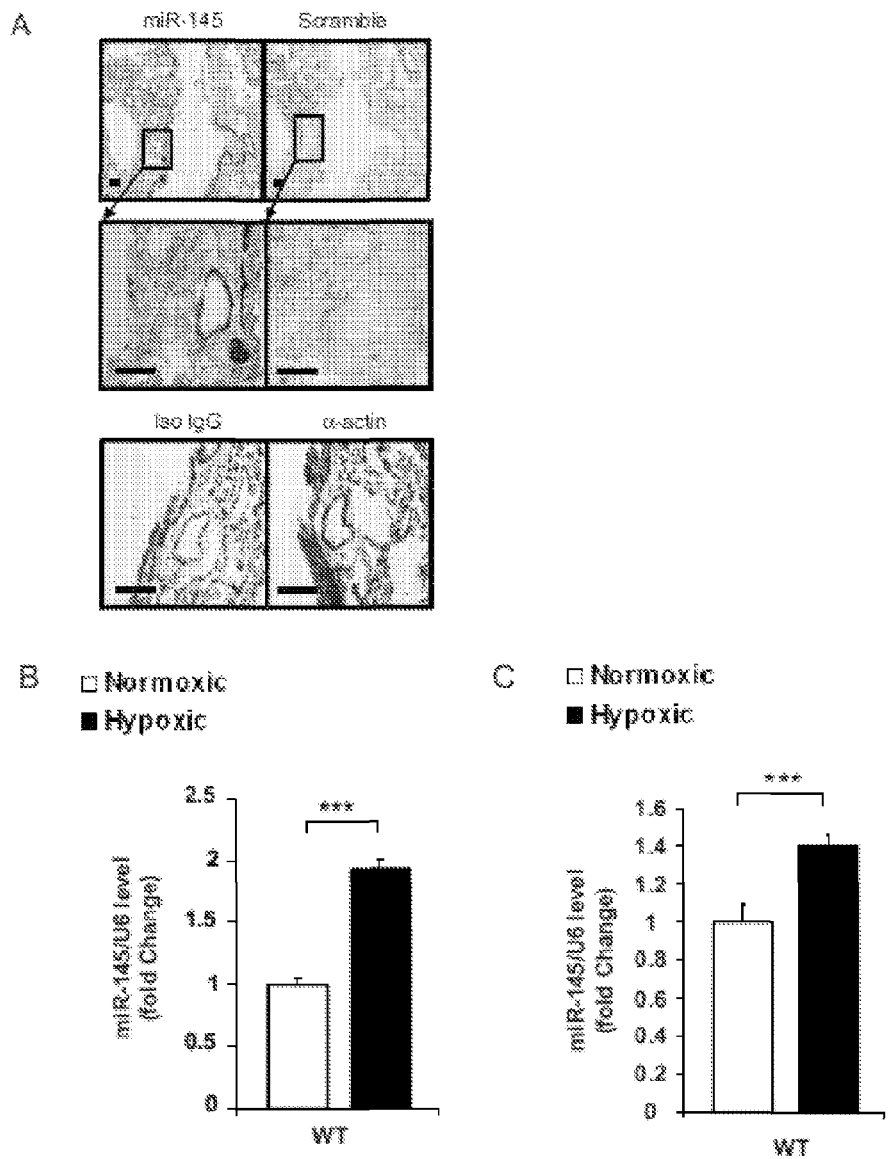
FIG. 2. MiR-145 localization in mouse lung section and expression in normoxic versus hypoxic mice. (A) In situ hybridization showing miR-145 localization in mouse lung. Paraffin sections were rehydrated and incubated with an anti-miR-145 or scramble probe as negative control. For co-localization, α-actin was detected in the same samples using an immunohistochemistry assay, with nonimmune isotype-IgG antibody as negative control. Images ×100 or ×400 magnification=50 q-PCR analysis of normoxic and 14 days hypoxic wild-type mice. Total RNA was extracted from the (B) total lung or (C) right ventricle, of normoxic (white bars) or hypoxic (black bars) 10 week-old mice. 6 mice/group were analyzed. Every sample was tested in triplicate. Results were normalized to U6 values and expressed as relative fold change, with an arbitrary value of 1 assigned to the control group. Data were analyzed using an unpaired t-test (***$p<0.001$ vs. control samples).
Figure 3:
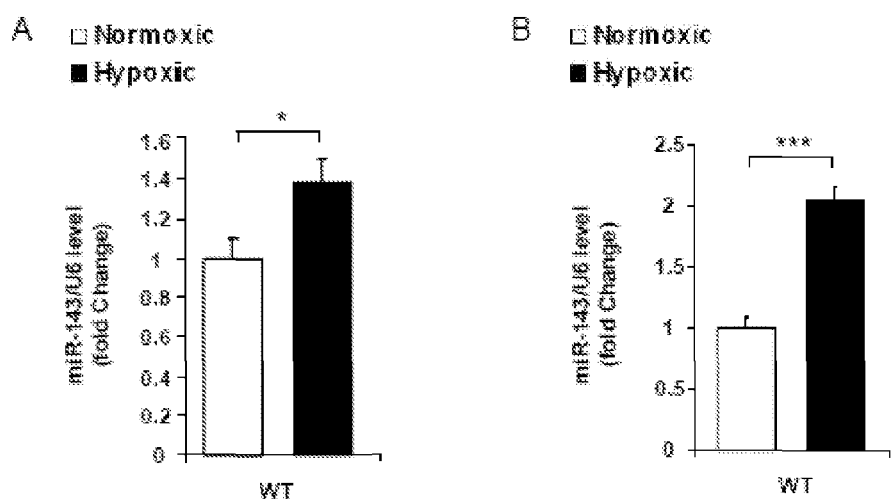
FIG. 3. MiR-143 in normoxic versus hypoxic mice. q-PCR analysis of normoxic and 14 days hypoxic wt mice. Total RNA was extracted from the (A) total lung or (B) the right ventricle, of normoxic (white bars) or hypoxic (black bars) 10 week old mice. 6 mice per group were analyzed. Each sample was tested in triplicate. Results were normalized to U6 values and expressed as relative fold change, with an arbitrary value of 1 assigned to the control group. Data were analyzed using an unpaired t-test (*$p<0.05$, ***$p<0.001$ vs normoxic samples).
Figure 4:
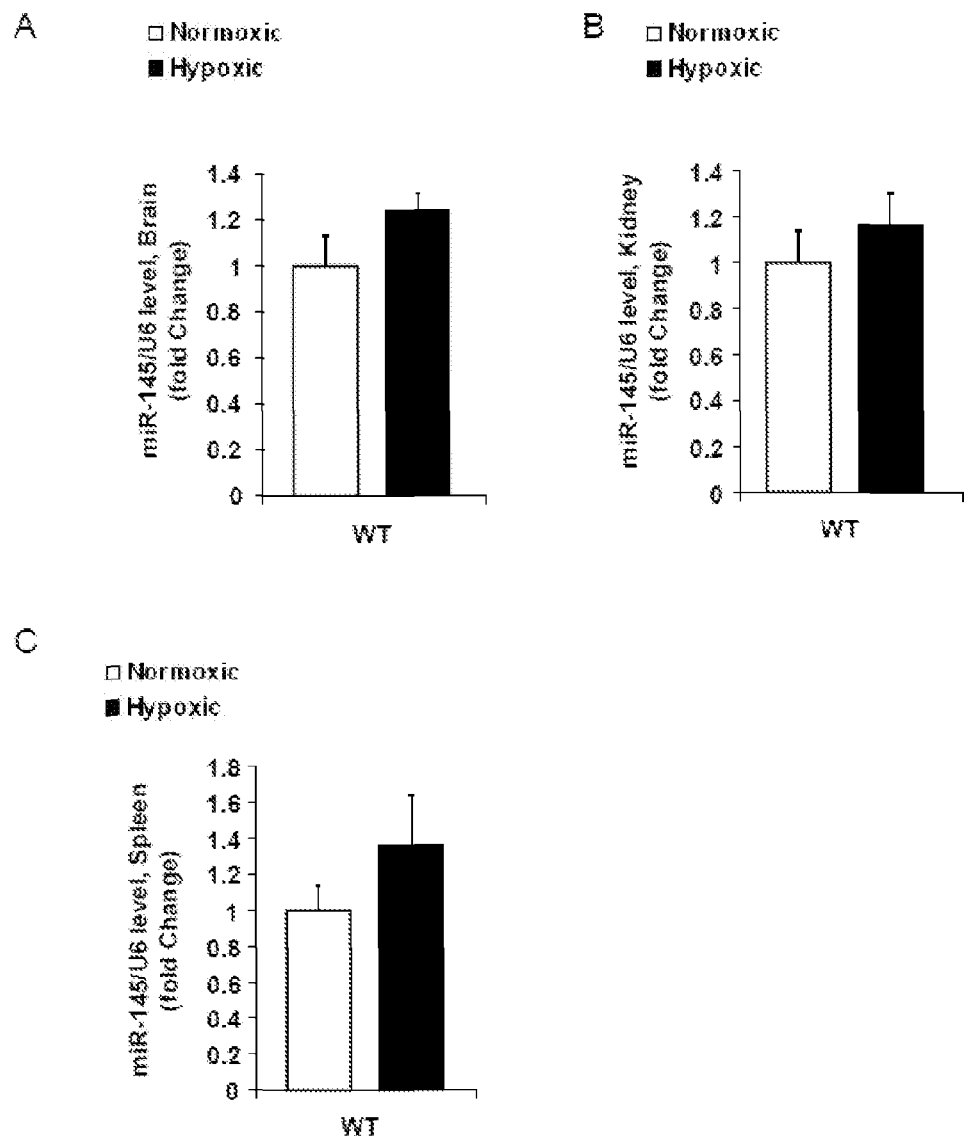
FIG. 4. MiR-145 expression in the brain, kidney and spleen of hypoxic wt mice. (A, B, C, respectively) of normoxic (white bars) or hypoxic (black bars) mice. Total RNA was extracted in quadruplicate from each organ and analyzed by q-PCR. Data were analyzed using a t-test but no significance was identified.
Figure 5:
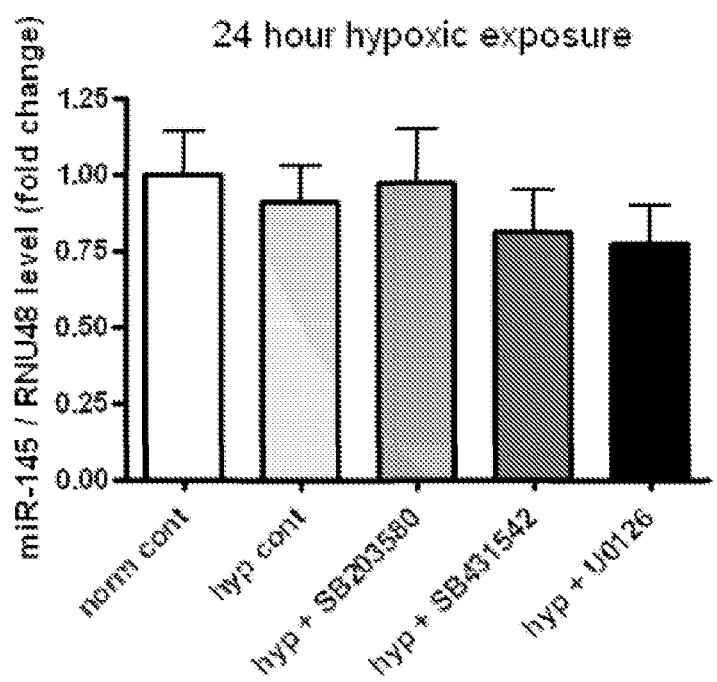
FIG. 5. MiR-145 expression in SMC exposed to 5% hypoxia in vitro. Primary distal pulmonary artery smooth muscle cells were exposed to (A) 24 h or (B) 72 h, 5% hypoxia in vitro and assessed for levels of miR145 at 24 with and without the presence of inhibitors SB203580 (p38 inhibitor-5 μM); SB431542 (TGF-β inhibitor 1 μM); U0126 (ERK inhibitor—1 μM).
Figure 5:
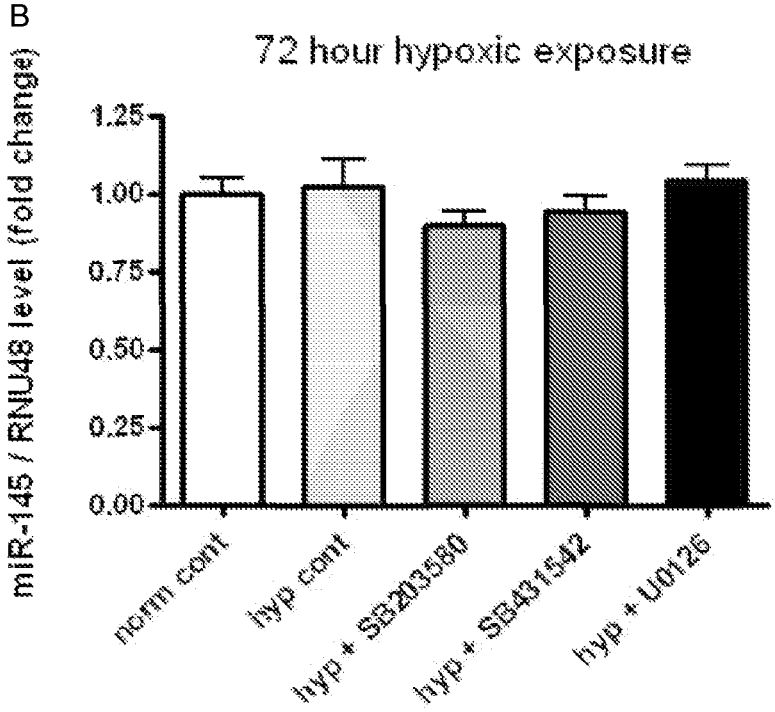

Elimination of miR-145 Expression Protects Against the Development of Pulmonary Arterial Hypertension in Mice To evaluate whether miR-145 was expressed in lung tissue, in situ hybridization was performed on lung tissue sections of wild-type (wt) mice, as described above. Positive staining for miR-145 was observed within the smooth muscle layer of vessels and bronchi in the lungs of the mice (FIG. 2A). To evaluate whether miR-145 expression was altered during response to injury, the expression of miR-145 was assessed by quantitative PCR in the total lung and the right ventricle from wt mice exposed to hypoxia for 14 days and this expression was compared to mice exposed to normoxic conditions. The analysis revealed a significant up-regulation of miR-145 in response to hypoxia both in lung and the right ventricle (FIG. 2B, C, respectively). miR-143 levels were also upregulated (FIG. 3). Analysis of miR-145 expression in the brain, kidney and spleen of the same animals did not reveal any dysregulation (FIG. 4). Thus, miR-145 is expressed in smooth muscle cells in the lung of mice and is up-regulated in response to hypoxia selectively in the lung. In isolated human distal pulmonary arterial SMC, changes in miR-145 at 24 h and 72 h exposure to hypoxia were not detected, suggesting complex regulation in vivo within the multicellular vascular compartment (FIG. 5).

Next, the effect of genetic ablation of miR-145 on the development of PAH was evaluated. MiR-145 knockout mice have previously been described (Xin et al. (2009) Genes Dev., Vol. 23: 2166-2178). Homozygous miR-145 −/− female mice or age-matched wild-type controls (strain C57BL6J/129SVEV, 8 weeks of age) were exposed to chronic hypoxia for 14 days or maintained in normoxic conditions and assessed at 10 weeks of age.

Eight week-old miR-145 knockout (miR-145 −/−) mice and control age-matched littermates were exposed to chronic hypoxia or maintained in normoxic conditions for 14 days and evaluated for the development of PAH at 10 weeks of age. For all the experiments, right systolic ventricular pressure (sRVP) was measured in mice under isoflurane (1.5% in $O_2$) anaesthesia via a needle advanced into the right ventricle trans-diaphragmatically. Systemic arterial pressure (SAP) was recorded via a cannula placed in the carotid artery as previously described (Keegan et al., 2001). Right ventricular hypertrophy (RVH) was determined as ratio of the right ventricular wall (RV) weight to the left ventricle plus septum (LV+S) weight. Lung sections were stained with Elastic-Van Gieson (EVG) stain and the percentage of remodeled vessels assessed in a blinded fashion as previously described (Keegan et al., 2001). The arteries were considered muscularized if they possessed a distinct double-elastic lamina visible for at least half the diameter in the vessel cross-section. 5 mice/group were analyzed for remodeling. Approximately 150 arteries from each lung section were assessed.

Figure 6:
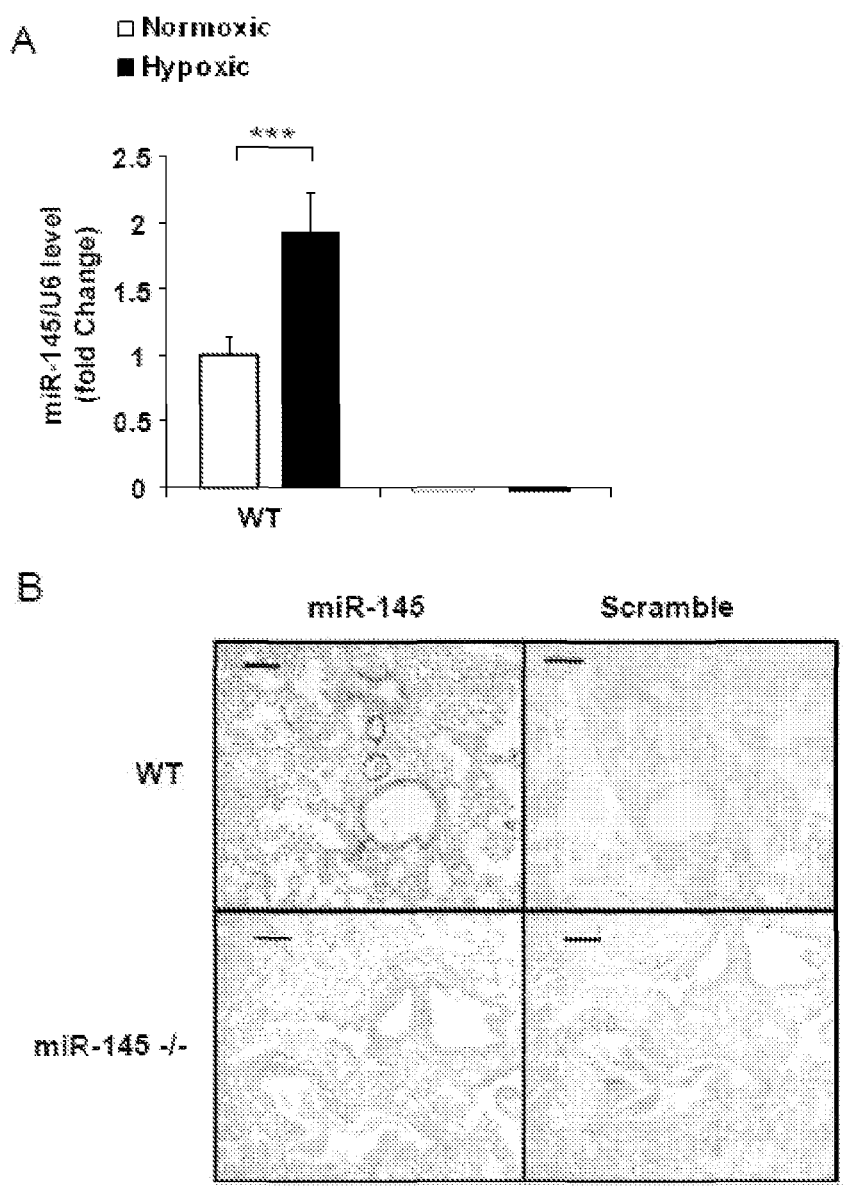
FIG. 6. Analysis of miR-145 expression in miR-145 −/− mice in comparison with wt mice. miR-145 ablation in ko mice was confirmed by (A) q-PCR and (B) in situ analysis. Images all ×100 magnification, scale bars=100 μm.
Figure 7:
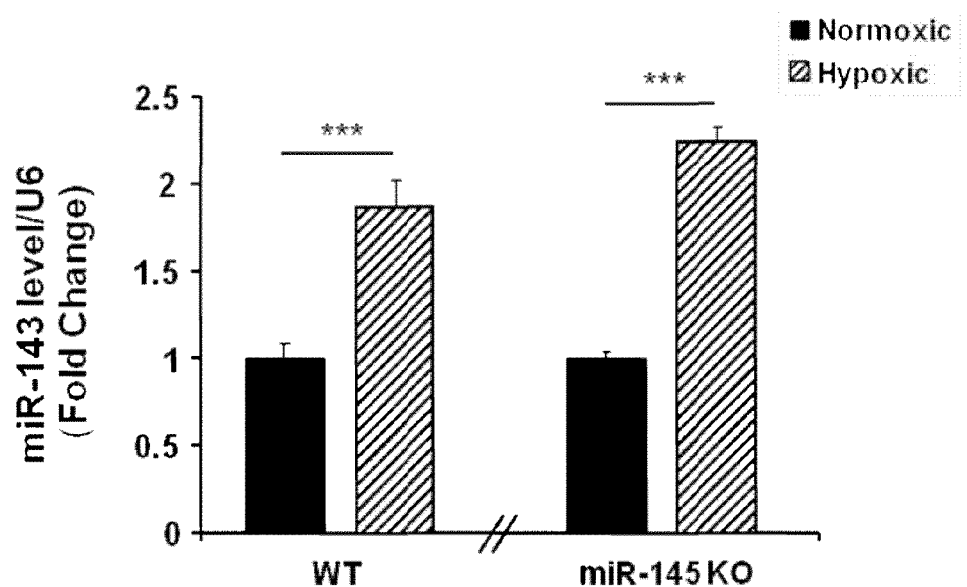
FIG. 7. MiR-143 expression in wild-type and miR-145 −/− mice in response to hypoxia. q-PCR analysis of normoxic and 14 days hypoxic wild-type (WT) and knockout (KO) mice. Total RNA was extracted from normoxic (black bars) or hypoxic (striped bars) 10 week-old mice. 6 mice/group were analyzed. Results were normalized to U6 values and expressed as relative fold change, with an arbitrary value of 1 assigned to the control group. Data were analyzed using a two-way ANOVA followed by Bonerroni's post-hoc test (***$p<0.001$ vs. control samples).

The absence of miR-145 expression in the knockout animals used in the study was confirmed by quantitative PCR (q-PCR) and in situ hybridization (FIG. 6). Since miR-145 is transcribed in its pri-miRNA form clustered with miR-143, the expression of miR-143 was also analyzed in wild-type and knockout animals under both normoxic and hypoxic conditions to ensure that miR-143 levels were not substantially altered in the lung following genetic ablation of miR-145 and in response to hypoxic insult. Q-PCR analysis of miR-143 expression in RNA extracted from the total lung of wild-type and miR-145 −/− mice showed no difference in response to hypoxia between wild-type and miR-145 −/− animals (FIG. 7). Thus, any changes in the development of PAH in response to hypoxia in miR-145 −/− were specific to the selective loss of miR-145.

Figure 8:
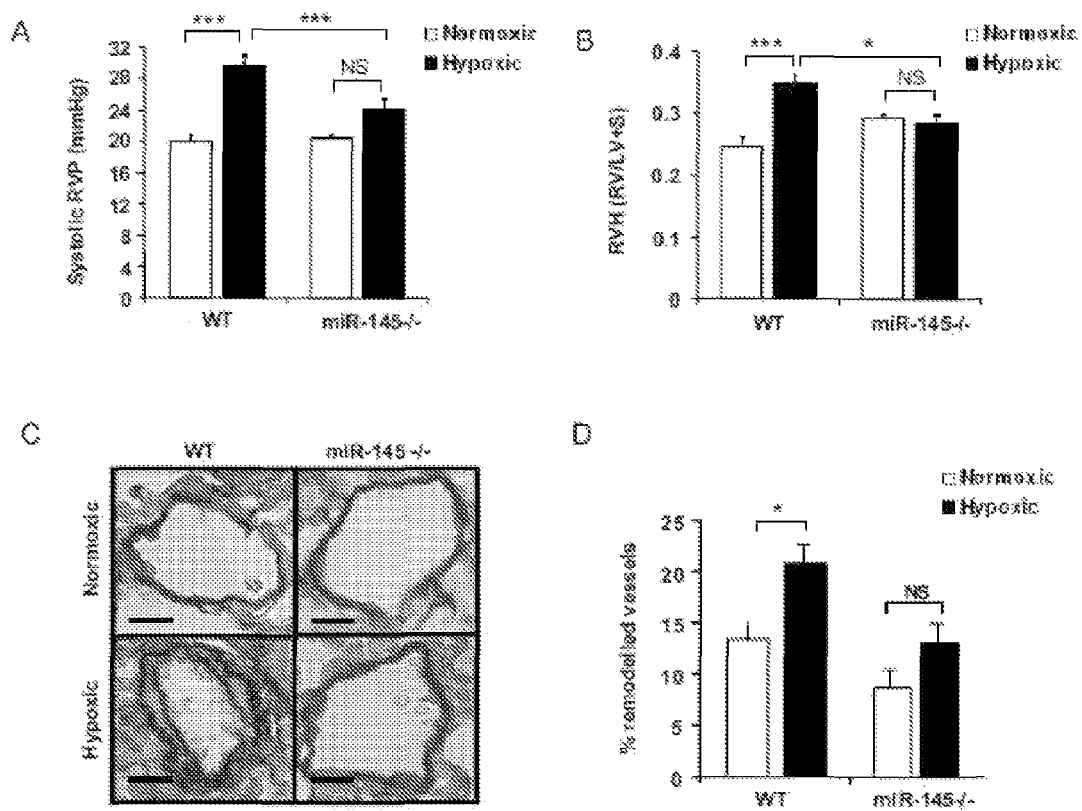
FIG. 8. Effect of miR-145 ablation on the development of PAH and vessel remodeling in mice. Assessment of (A) systolic right ventricular pressure (sRVP, n=9-10) and (B) right ventricular hypertrophy (RVH, n=9-10). (C) Representative pulmonary arteries stained with elastic-Van Gieson. Images all 400× magnification, scale bars=50 μm. (D) Pulmonary arterial remodeling from both normoxic and hypoxic wild-type (WT) and miR-145 −/− mice (n=5). Mice were subjected to hypoxia for 14 days. n, number of mice. Data were analyzed using a two-way ANOVA followed by Bonferroni's post-hoc test (*$p<0.05$ vs. WT normoxic mice).

Next, the development of PAH in wild-type and miR-145 −/− mice was quantified. In wild-type mice, a significant and expected increase in systolic RVP and RVH was observed (FIG. 8A, B). In contrast, miR-145 −/− animals displayed no increase in systolic RVP or RVH (FIG. 8A, B). Interestingly, there was no difference in baseline systolic RVP or RVH between wild type and miR-145 −/− mice (FIG. 8A, B). The measurements are as noted in Tables 1 and 2:

TABLE 1

Ventricle weight in WT and miR-145 −/− mice.

| Group | RV (mg) | LV + S (mg) | RV/LV + 2 |
|---|---|---|---|
| WT Normoxic | 22.06 ± 1.13 | 85.12 ± 1.24 | 0.26 ± 0.015 |
| WT Hypoxic | 25.71 ± 0.84 | 73.69 ± 1.77 | 0.35 ± 0.012*** |
| miR-143 −/− Normoxic | 18.60 ± 1.25 | 69.74 ± 3.08 | 0.27 ± 0.014 |
| miR-145 −/− Hypoxic | 19.21 ± 0.85 | 68.63 ± 1.92 | 0.28 ± 0.014††† |

Right ventricle (RV) weight, left ventricle plus septum (LV + S) weight and RV/LV + S ratio.
***$P < 0.001$ cf. WT normoxic mice;
†††$P < 0.001$ cf. WT hypoxic mice; Data expressed as mean + SEM. n = 9-10.

TABLE 2

Haemodynamics in WT and miR-145 −/− mice, normoxic and hypoxic.

| Parameter | WT Normoxic | WT hypoxic | KO Normoxic | KO Hypoxic |
|---|---|---|---|---|
| sRVP, mmHg | 20.00 ± 0.80 | 29.71 ± 1.16*** | 21.21 ± 0.61 | 27.07 ± 1.38††† |
| SAP, mmHg | 83.22 ± 1.55 | 94.01 ± 2.91 | 71.34 ± 8.14*** | 70.92 ± 5.59*** |
| Heart rate, bpm | 329.42 ± 8.92 | 329.18 ± 12.66 | 325.88 ± 6.67 | 342.08 ± 14.78 |

Systolic right ventricular pressure(sRVP), systemic systolic arterial pressure (SAP) and heart rate measurements in normoxic and chronically hypoxic female WT and miR-145 −/− mice.
***$P < 0.001$ cf. WT normoxic mice;
†††$P < 0.001$ cf. WT hypoxic mice; Data expressed as mean + SEM. n = 6-10.

Histological analysis showed the presence of pulmonary vascular remodeling in small pulmonary arteries (PAs) of wild-type animals following exposure to hypoxia but such remodeling was reduced in lungs harvested from miR-145 −/− animals, a finding confirmed by quantitative scoring (FIG. 8C, D). Therefore, genetic ablation of miR-145 protects mice against the development of PAH in response to hypoxia.

Figure 9:
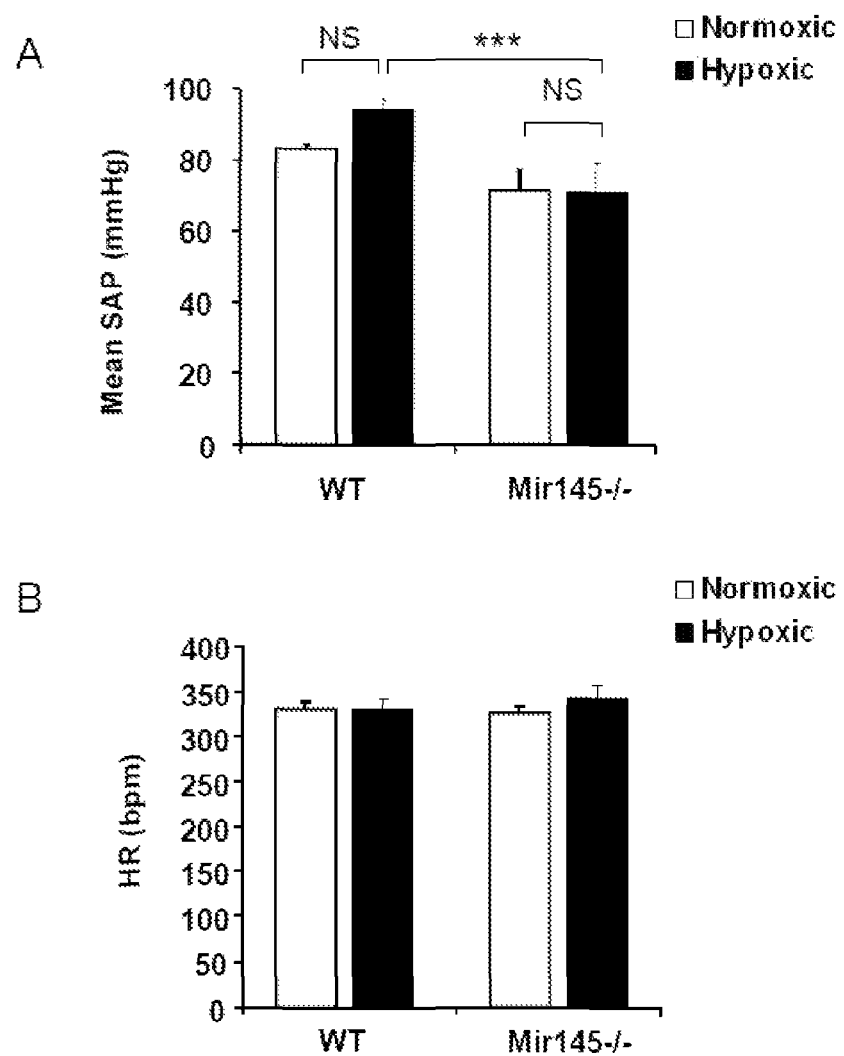
FIG. 9. Assessment of (A) systemic arterial pressure (SAP, n=6-9), and (B) heart rate (HR, n=6-10) in wild-type and miR-145 −/− mice subjected to normoxic or hypoxic conditions. Mice were subjected to hypoxia for 14 days. n, number of mice. Data were analyzed using a two-way ANOVA followed by Bonferroni's post-hoc test (*$p<0.05$, $p<0.005$, *$p<0.001$ vs. wild-type normoxic mice).

The mean SAP was lower in miR-145 −/− mice compared to controls, as expected and consistent with previously published work (Elia et al., 2009; Xin et al., 2009). Neither the wild-type or miR-145 −/− mouse SAP were altered by exposure to hypoxia (FIG. 9A) and no changes were observed in the heart rate (HR) of the wt or miR-145−/− mice exposed to hypoxia (FIG. 9B).

The results of this series of experiments show that miR-145 is expressed exclusively in the smooth muscle cell compartment in lungs taken from mice subjected to normoxic or hypoxic conditions. In the hypoxic mouse model, miR-145 levels are elevated as compared to controls and genetic ablation of miR-145 prevents the development of PAH. A functional analysis of the vasculature of miR-145 −/− mice revealed a reduced response to hypoxia: when these mice were exposed to hypoxia for two weeks, systolic pressure did not show a significant rise as in wild-type mice. A similar result was obtained for right ventricular hypertrophy. In addition, the percentage of remodeled vessels was significantly reduced in the knockout animals, strongly suggesting a protective role for miR-145 ablation in PAH development. This effect occurred in the absence of any modulation of miR-143, thus confirming the importance of miR-145 in the development of PAH. Thus, these findings suggest that miR-145 may be a viable therapeutic target for designing treatments for PAH.

Example 11

Figure 10:
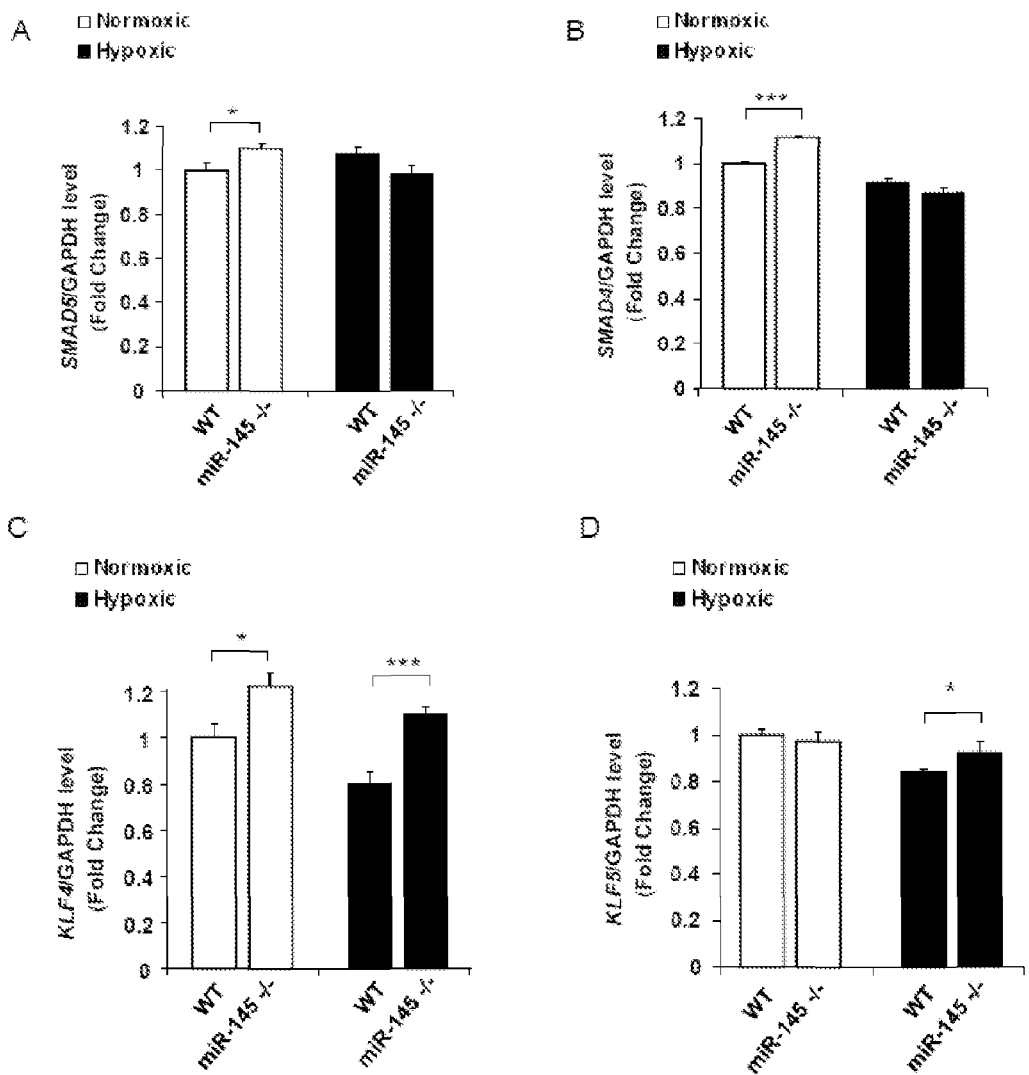
FIG. 10. Analysis of miR-145 selected targets. The expression level of (A) SMAD5, (B) SMAD4, (C) KLF4 and (D) KLF5 was assessed by q-PCR in the total lung of wt and miR-145 −/− mice, normoxic and hypoxic. Data were analyzed using a one-way ANOVA followed by Bonferroni's post-hoc test ($*p<0.05$, $***p<0.001$).
Figure 11:
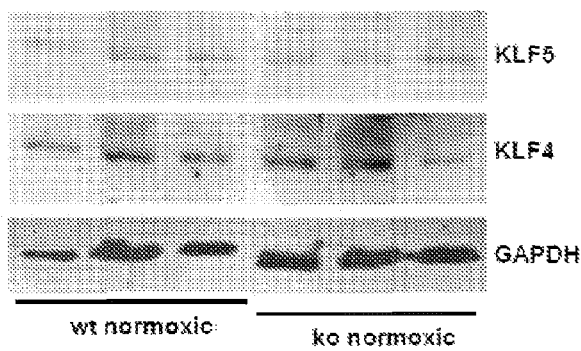
FIG. 11. Analysis of KLF4 and KLF5 protein expression level in WT and miR-145 −/− hypoxic female mice. (A, D) The expression level of KLF4 and KLF5 was assessed by western blot in the total lung of WT and miR-145 −/− mice exposed to chronic hypoxia for 14 days. 4 mice/group were analyzed, and the intensity of the western blot bands was measured using a specific software (Scion Image software). The resulting quantification bars are represented in graphs in (B), (C), (E) and (F). Results were normalized to GAPDH values and expressed as fold increase, with an arbitrary value of 1 assigned to the WT group. Data were analyzed using an unpaired t-test. $**p<0.005$ cf. wt mice.
Figure 11:
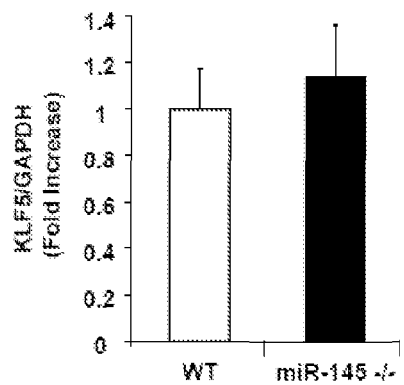
Figure 11:
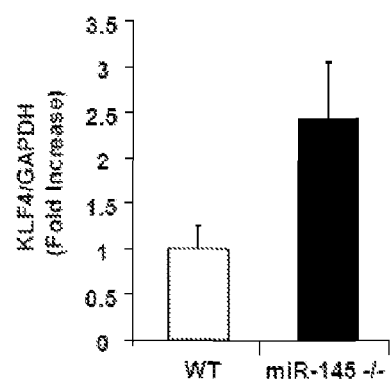
Figure 11:
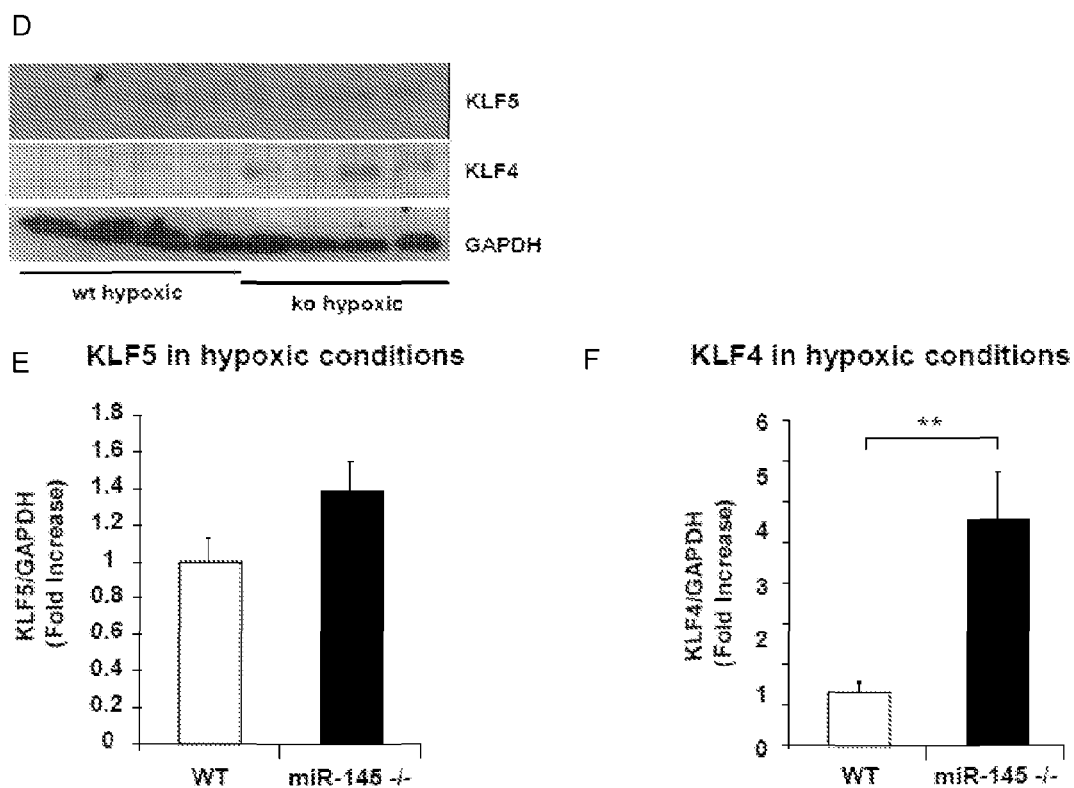

Analysis of miR-145 Predicted Targets in the Lungs of miR-145−/−Mice Compared to Controls In order to verify the effect of miR-145 ablation on gene and protein expression, several miR-145 gene targets, already validated in the literature or identified using TargetScan and PicTar prediction algorithms and selected for their potential involvement in PAH, were analyzed by q-PCR in lung tissue of wt and miR-145 ko animals. They included KLF4 and KLF5 (Krueppel-like factor 4 and 5), both involved in SMC proliferation and differentiation, and SMAD4 and SMAD5, signaling intermediaries for the TGF-β super-family. Analysis of RNA revealed a significant up-regulation of both SMAD4 and WADS in miR-145 −/− normoxic mice in comparison with wt normoxic mice (FIG. 10A, B). KLF4 was elevated both in normoxic and hypoxic miR-145 −/− mice while KLF5 expression was significantly up-regulated in wt hypoxic versus miR-145 −/− hypoxic mice (FIG. 10C, D). The western blot analysis of KLF4 protein expression in WT and KO animals in hypoxic conditions confirmed the significant upregulation of this target, whereas no significant changes were observed in normoxia (FIG. 11). In contrast, the KLF5 protein level was not significantly up-regulated in the same samples both in normoxic and hypoxic conditions (FIG. 11).

Example 12

Microarray Analysis of Gene Expression Profile in the PAs of miR-145 −/− Mice in Comparison with WT Animals Global transcriptome analysis was performed with 6 samples from each of the miR-145−/− hypoxic, WT hypoxic miR-145 −/− normoxic and WT normoxic groups. Potential miR-145 targets with 3'UTR miRNA binding regions as predicted in at least 3 of the databases in miRWalk and significant false discovery rates in the miR-145 −/− hypoxic vs WT hypoxic comparison were selected for further analysis. Ingenuity pathway analysis software and the Database for Annotation, Visualization and Integrated Discovery (DAVID) were used to select targets that are present in pathways relevant to pulmonary hypertension. A total of 13 targets were selected for validation by real time PCR using these selection criteria (Table 3).

TABLE 3

Microarray data for targets selected for validation.

| PROBE_ID | SYMBOL | ACCESSION | False discovery rate | Fold change | miR-145 target? |
|---|---|---|---|---|---|
| | | | KO hyp vs WT hyp | | |
| ILMN_2424060 | ACE | NM_207624.4 | 1.41e−04 | 2.15 | Validated |
| ILMN_2636424 | ITGBL1 | NM_145467.1 | 8.02e−05 | 2.06 | Predicted |
| ILMN_2857748 | WIF1 | NM_011915.1 | 2.04E−04 | 1.97 | Predicted |
| ILMN_2759365 | ANGPTL4 | NM_020581.1 | 1.73E−03 | 1.70 | Predicted |
| ILMN_2601155 | FRZB | NM_011356.4 | 3.82E−03 | 1.62 | Predicted |
| ILMN_3147944 | AP2B1 | NM_001035854.2 | 6.35E−03 | 1.53 | Predicted |
| ILMN_2909150 | CTGF | NM_010217.1 | 2.97E−02 | 1.40 | Predicted |
| ILMN_1228221 | TTN | NM_176926.2 | 1.20E−02 | −1.37 | Predicted |
| ILMN_2596479 | CAMK2A | NM_177407.3 | 8.04E−03 | −1.43 | Predicted |
| ILMN_2588759 | APH1a | NM_146104.2 | 1.99E−03 | −1.63 | Predicted |
| ILMN_2977404 | TMOD1 | NM_021883.1 | 2.07E−03 | −2.01 | Predicted |
| | | | KO hyp vs WT nor | | |
| ILMN_2543173 | DAB2 | AK002850 | 3.22E−02 | 1.39 | Validated |
| | | | WT.hyp.vs.wt.nor | | |
| ILMN_2630605 | FSCN1 | NM_007984.2 | 3.09E−04 | 2.34 | Validated |

Figure 12:
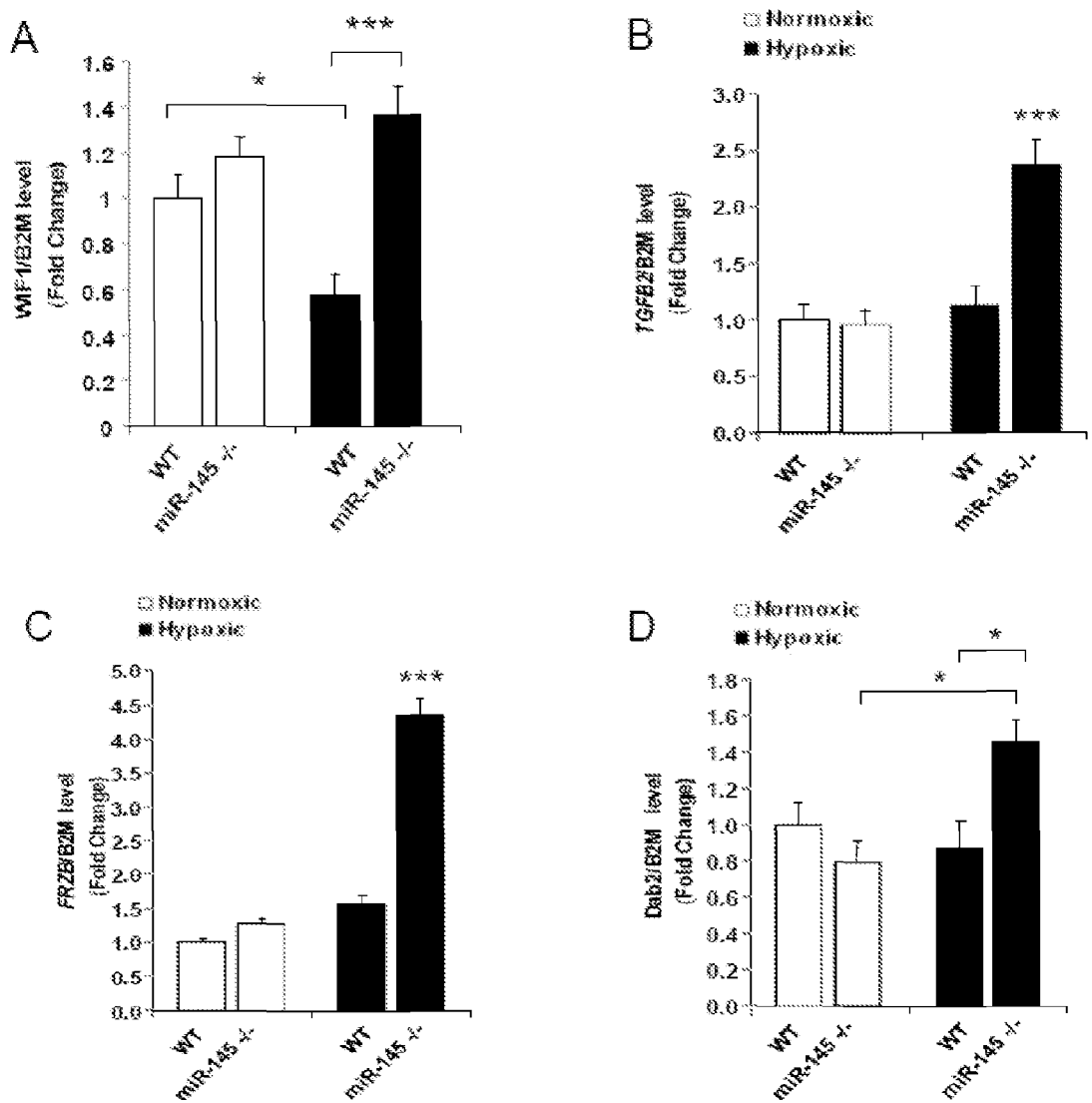
FIG. 12. Validation of microarray data. The expression level of (A) WIF1, (B) TGFB2, (C) FRZB, (D) DAB2, (E) ACE, (F) FSCN1, (G) CTGF, (H) Angpl14, (I) AP2B1 and (J) ITGBL1H, was assessed by q-PCR in pulmonary artery of wt and miR-145 −/− mice, normoxic and hypoxic. Data were analyzed using a one-way ANOVA followed by Bonferroni's post-hoc test ($*p<0.05$, $***p<0.001$).
Figure 12:
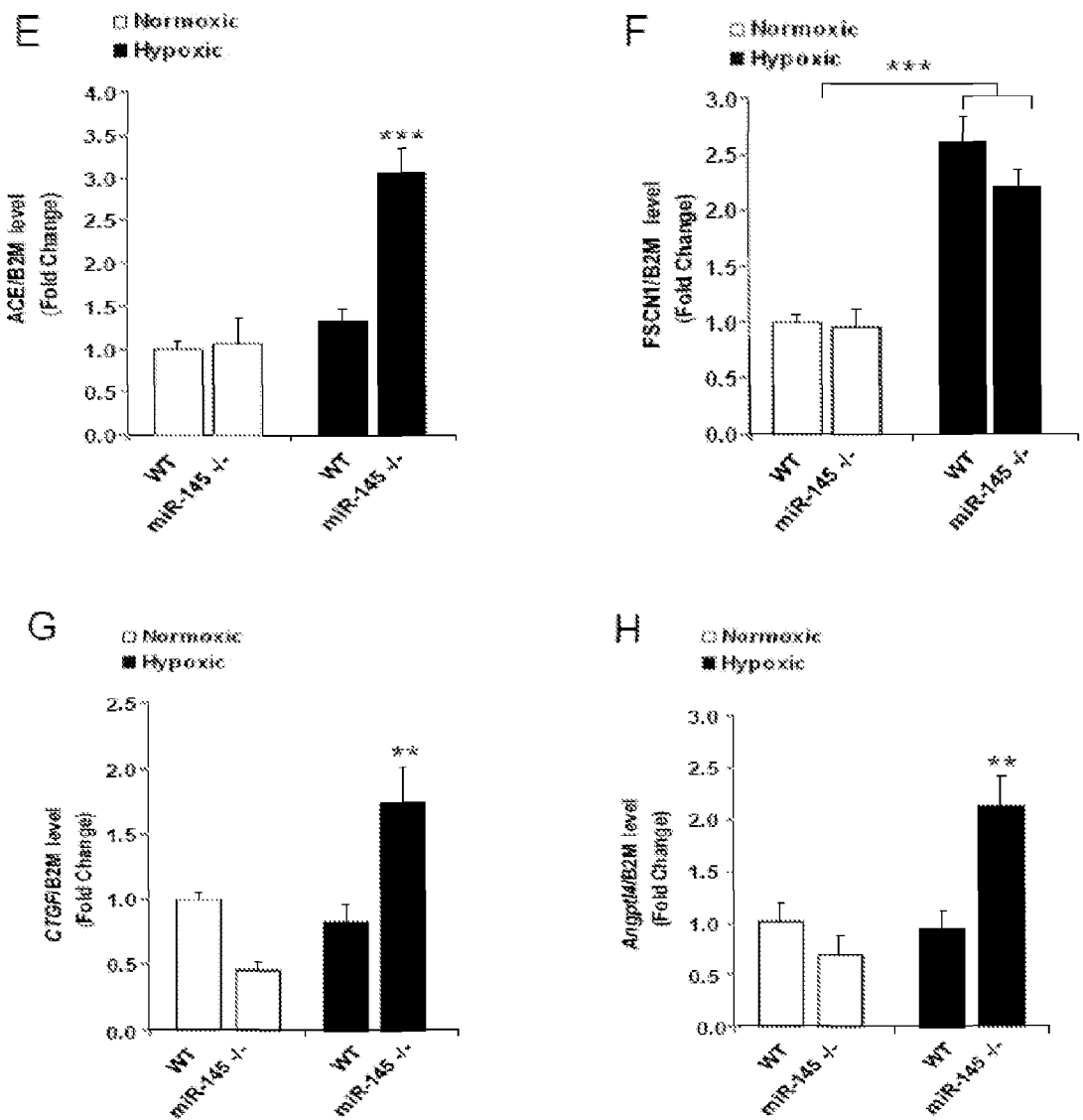
Figure 12:
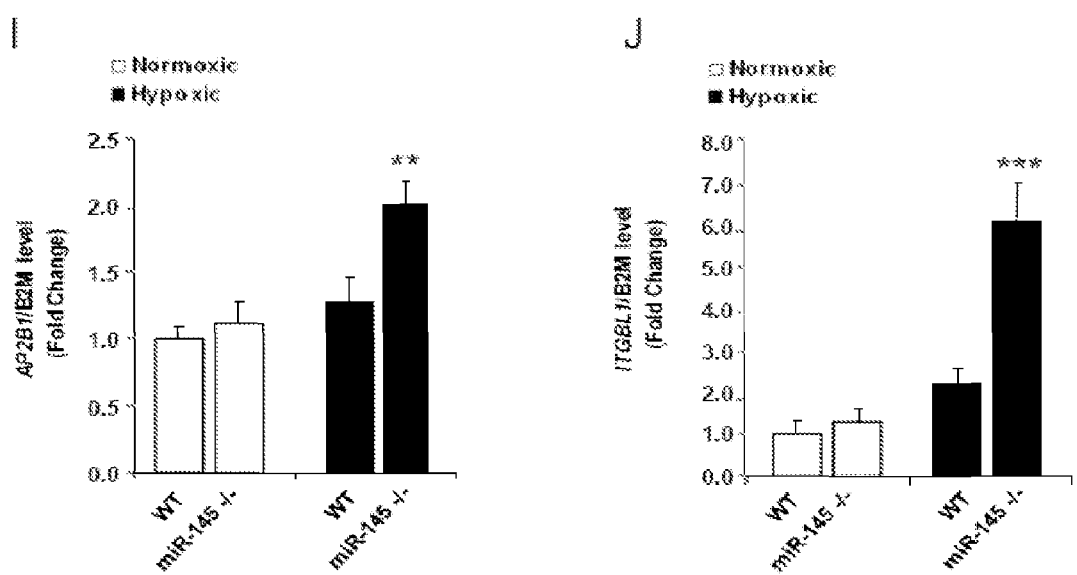

The validated miR-145 targets FSCN1, DAB2 and ACE were selected for further analysis (Cheng et al., 2009; Boettger et al., 2009; Kano et al., 2010; Xu et al., 2009). Real time PCR validated 10 of the targets selected from the microarray (FIG. 12). The WT hypoxic group showed significantly increased expression versus all other groups for 7 of the targets TGFB2, FRZB, ACE, CTGF, ANGPTL4, AP2B1 and ITGBL1 (FIG. 12). Further, the real time PCR data reflected the changes between groups observed in the microarray for W1F1, CAMK2A, TTN, ACE, DAB2 and FSCN1 (Table 3) and showed that these changes were significant (FIG. 12). The changes observed in the microarray were not validated for TMOD1 and APH1A (not shown). The validated targets were categorized into 5 groups: inhibitors of wnt signalling (W1F1, FRZB, DAB2), regulation of actin cytoskeleton (FSCN, TTN), transcriptional regulation (CAMK2A), cell adhesion (ITGBL1, CTGF) and endothelial function (ACE, ANGPTL4). Further analysis from the array data revealed marked changes in many components of the WNT signaling pathway (Table 4).

Thus, a whole transcriptome microarray study on isolate pulmonary arteries was used to quantify the transcriptional response to hypoxia. KLF4 and 5 expression correlate with miR-145 regulation, with a significant up-regulation of both these targets in hypoxic miR-145 knockout mice. Three validated targets from the WT hypoxic vs miR145−/− hypoxic comparison inhibit canonical wnt/β-catenin signalling. WIF1 and FRZB bind to Wnt proteins in the extracellular space and prevent ligand-receptor interactions (Leyns et al., 1997; Hsieh et al., 1999; Jiang et al., 2009; Baldin et al., 1993; Baranwal et al., 2009), while DAB2 stabilizes phosphorylated axin and attenuates Wnt/β-catenin signaling by increasing proteasomal degradation of β-catenin (Jiang et al., 2009). These factors inhibit wnt signaling leading to decreased expression of wnt target genes, such as cyclin D1 (CCND1) and E cadherin (CDH), which were also found downregulated in the miR145−/− hypoxic group (Table 2). Downregulation of CDH and CCND1 can cause cytoskeletal reorganisation

TABLE 4

Significant targets from the microarray that are components of the wnt pathway.

| PROBE_ID | SYMBOL | ACCESSION | False discovery rate | Fold change | Role in wnt signaling |
|---|---|---|---|---|---|
| *KO.hyp.vs.WT.hyp* | | | | | |
| ILMN_2857748 | WIF1 | NM_011915.1 | 0.0002 | 1.9685 | Negative regulator of canonical wnt signaling |
| ILMN_1225196 | TGFB2 | NM_009367.2 | 0.0003 | 1.8467 | Negative regulator of canonical wnt signaling |
| ILMN_2604282 | SFRP1 | NM_023653.4 | 0.0033 | 1.6829 | Negative regulator of canonical wnt signaling |
| ILMN_1258734 | WNT2 | NM_023653.4 | 0.0165 | 1.6295 | Positive modulator of wnt signaling |
| ILMN_2601155 | FRZB | NM_011356.4 | 0.0038 | 1.6218 | Negative regulator of canonical wnt signaling |
| ILMN_1215252 | BMP4 | NM_007554.2 | 0.0111 | 1.5668 | Expression is inhibited by wnt |
| ILMN_2588227 | FN1 | NM_010233.1 | 0.0116 | 1.5155 | Positive modulator of wnt signaling |
| ILMN_2737710 | TIAM1 | NM_009384.2 | 0.0232 | 1.5102 | Positive modulator of wnt signaling. |
| ILMN_1214602 | SFRP2 | NM_009144.1 | 0.0350 | 1.3971 | Negative regulator of canonical wnt signaling |
| ILMN_2686745 | RGS12 | NM_173402.1 | 0.0146 | −1.4291 | Positive modulator of wnt signaling |
| ILMN_2450384 | VEGFB | NM_011697.2 | 0.0263 | −1.4756 | wnt target gene |
| ILMN_2753422 | GNAO1 | NM_010308.3 | 0.0092 | −1.5804 | Positive modulator of wnt signaling |
| *KO.hyp.vs.WT.nor* | | | | | |
| ILMN_1221594 | PPARG | NM_011146.2 | 0.0090 | 1.5400 | wnt target gene |
| ILMN_2669793 | CCND1 | NM_007631.2 | 0.0229 | −1.4080 | wnt target gene |
| *WT.hyp.vs.wt.nor* | | | | | |
| ILMN_3121255 | VEGFA | NM_001025250.2 | 0.0255 | 1.4672 | wnt target gene |
| ILMN_2889641 | WNT4 | NM_009523.1 | 0.0321 | −1.4181 | Positive modulator of wnt signaling |
| *KO.hyp.vs.KO.nor* | | | | | |
| ILMN_2789692 | WNT7b | NM_009528.2 | 0.0018 | −1.7822 | Positive modulator of wnt signaling |
| ILMN_2628629 | CDH1 | NM_009864.2 | 0.0010 | −1.8535 | wnt target gene | and decreased proliferation respectively (Baldin et al., 1993; Baranwal et al., 2009). Therefore, inhibition of wnt/β-catenin signaling may contribute to the phenotype observed in hypoxia in the miR145-/- mice.

Example 13

Quantification of the Development of PAH in Wt Mice Treated with a miR-145 antimiR in Comparison with Controls and Wt Mice Treated with a miR-143 antimiR To determine if the protective effect against the development of PAH observed in miR-145 ablated mice in response to chronic hypoxia can be replicated by pharmacological manipulation of miR-145, LNA antimiRs were used.

The LNA antimiRs were 16 nucleotides in length targeting base 2-17 of mature miR-145 (SEQ ID NO: 13) or mature miR-143 (5'-TACAGTGCTTCATCTC-3'; SEQ ID NO: 14) and were as fully phosphorothiolated oligonucleotides, perfectly complementary to the 5' region of either miR-143 or miR-145 and were synthesized as a mixer of LNA and DNA. The LNA control oligonucleotide (scramble) consisted of a sequence directed against a *C. elegans* specific miRNA with a comparable LNA/DNA content. AntimiR and control oligonucleotides were administered to female C57B16 mice (8-10 weeks old) via subcutaneous injection (25 mg/kg in 0.2 ml saline). Mice were injected with oligonucleotide or vehicle on days 1 and 8 of the 14 day hypoxic exposure.

Figure 13:
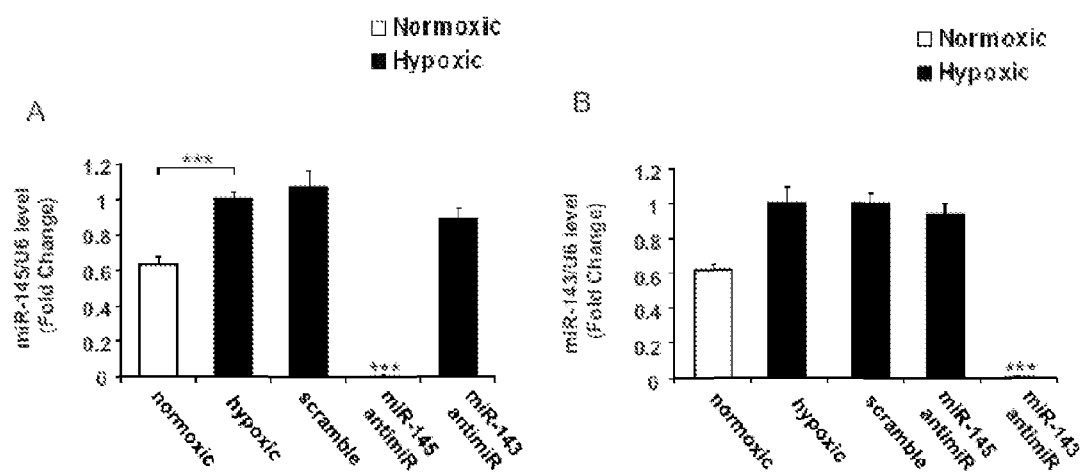
FIG. 13. Selective knock-down of miR-145 or miR-143 obtained after the injection of an antimiR miRNA specific. 8 week old female mice were injected subcutaneously with an antimiR perfectly complementary to the 5' region of either the mature miR-143 or miR-145 sequence and subjected to chronic hypoxic for 14 days. They received a second injection after 8 days of hypoxia. After 14 days, mice were sacrificed and total RNA extracted from the lung. (A) miR-145 and (B) miR-143 expression in normoxic vehicle treated animals, hypoxic vehicle treated animals, and hypoxic animals injected with a scramble, a miR-145 or a miR-143 antimiR. (C)-(F) Northern blot analysis of the same RNA assessed by q-PCR, showing (C)-(D) miR-145 or (E)-(F) miR-143 expression level. Data were analyzed using a one-way ANOVA followed by Bonferroni's post-hoc test ($*p<0.05$, $***p<0.001$. miR-145 and miR-143 down-regulation is statistically significant versus all the other groups.).
Figure 13:
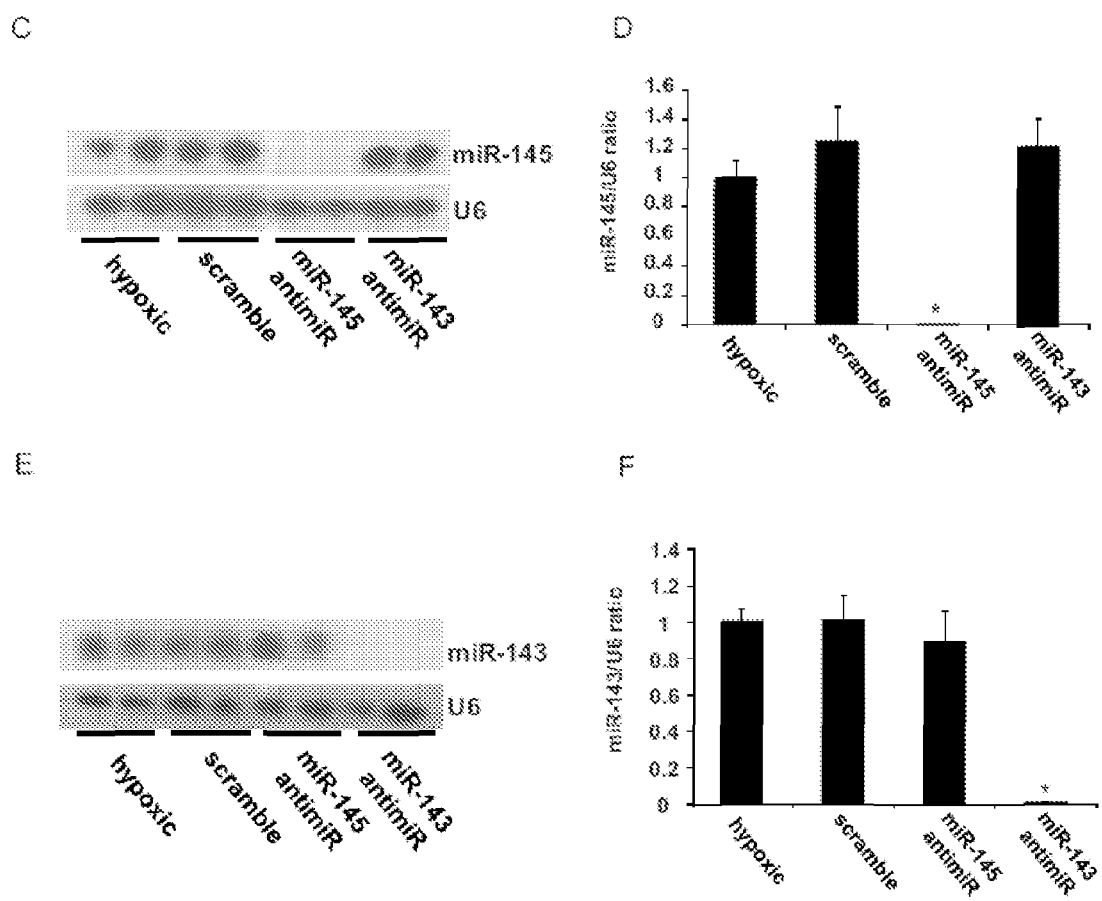
Figure 14:
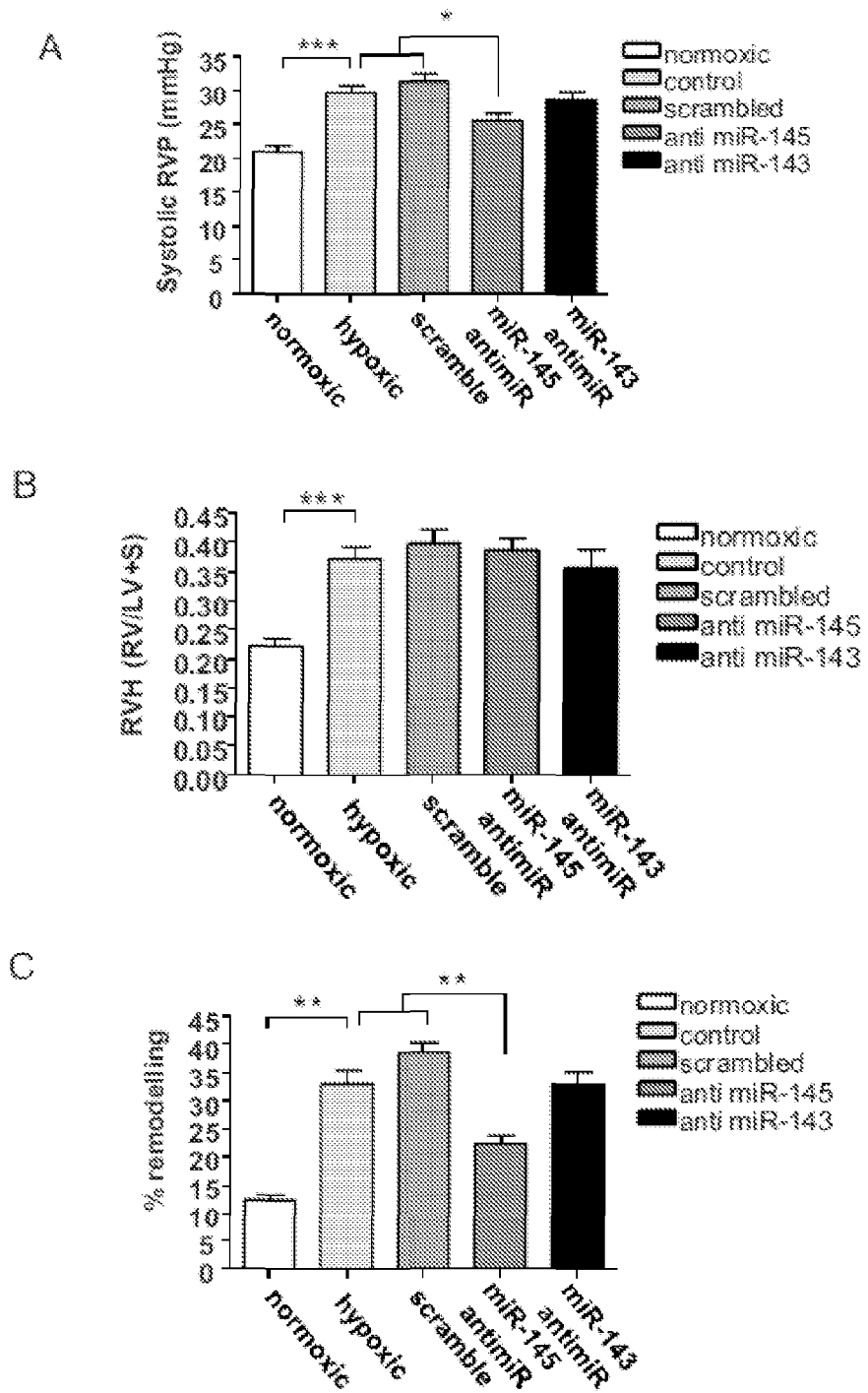
FIG. 14. Effect of miR-145 or miR-143 knock-down on the development of PAH and vessel remodelling in mice. Assessment of (A) systolic right ventricular pressure (sRVP, n=6-10), (B) right ventricular hypertrophy (RVH n=7-13) in C57B16 mice treated with an antimiR specific for miR-145 or miR-143, scrambled antimiR, or vehicle and exposed to chronic hypoxia for 14 days. (C) Pulmonary arterial remodeling measured in the same groups (n=4). n=number of mice. Data were analyzed using a one-way ANOVA followed by Bonferroni's post-hoc test ($*p<0.05$, $p<0.005$, $*p<0.001$). (D) Representative pulmonary arteries stained with elastic-Van Gieson. Images all ×40 magnification, scale bars=20 μM.
Figure 14:
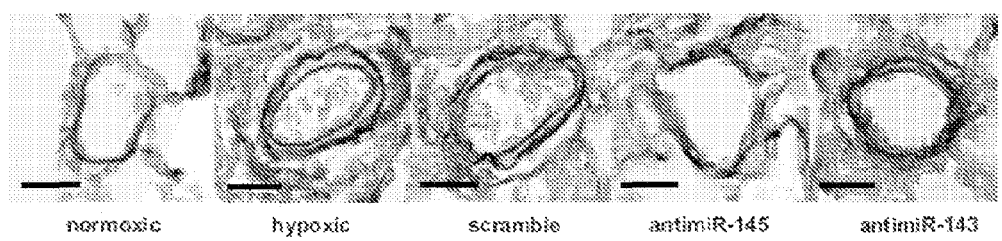
Figure 15:
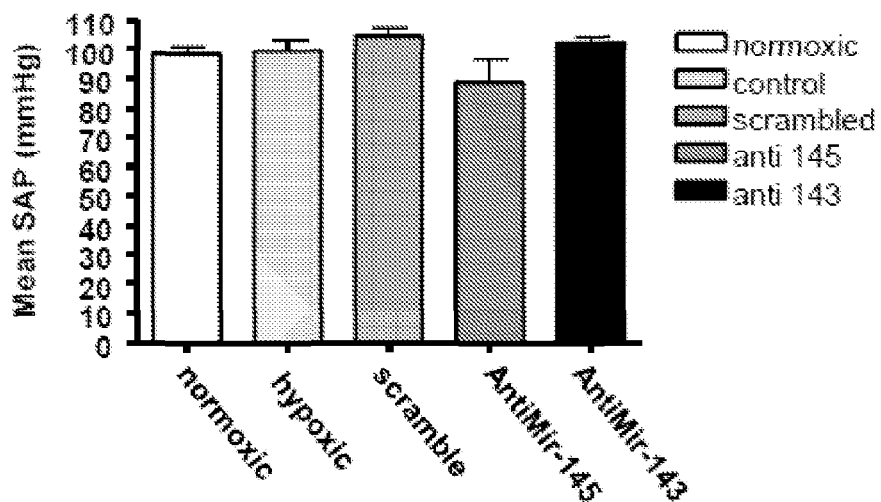
FIG. 15. Assessment of (A) systemic arterial pressure (SAP, n=6-8) and (B) heart rate (HR, n=7-13) in vehicle-treated normoxic mice and hypoxic mice injected with vehicle, scrambled, miR-145 or miR-143 antiMir. Data were analyzed using a one way ANOVA followed by Bonferroni's post-hoc test.
Figure 15:
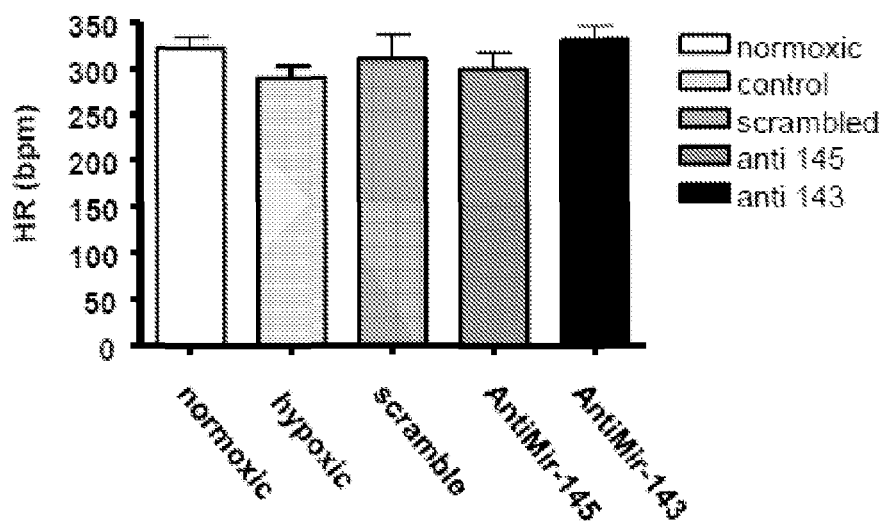

Eight-week old female C571316 mice were injected subcutaneously with an antimiR specific for miR-145 or miR-143 and then exposed for 2 weeks to chronic hypoxia and compared to vehicle- and scramble-treated mice. A second dose was injected at day 8 of hypoxic exposure. The selective and substantial down-regulation of miR-145 or miR-143 in the treated animals was confirmed in the lung by q-PCR (FIG. 13A, B). Scramble-treated mice showed no change in the expression of both miR-143 and miR.145 (FIG. 13A, B). Northern blot confirmed selective downregulation (FIG. 13C-F) The development of PAH in treated mice in comparison with controls was then evaluated. In vehicle treated hypoxic mice a significant and expected elevation in systolic RVP and RVH in comparison with vehicle treated normoxic mice was observed (FIG. 14). The same effect was observed in scramble-treated and antimiR-143 animals, however, mice treated with antimiR to miR-145 showed a significant reduction in systolic RVP (FIG. 14A). No changes were observed in RVH and SAP in antimiR-145 or antimiR-143 treated mice (FIG. 14B). Histological analysis showed a significant reduction of pulmonary vascular remodeling in small PAs of antimiR-145 treated mice exposed to chronic hypoxia in comparison with the percentage of remodeling observed in vehicle- or scramble-treated mice exposed to hypoxia (FIG. 14C, D). These data show that selective pharmacological manipulation of miR-145, but not miR-143, prevents the development of PAH in mice exposed to hypoxia. No changes in mean SAP were observed (FIG. 15A). No changes across the groups were observed in the HR (FIG. 15B).

Example 14 miR-145 Expression is Elevated in Lung Tissue of Human Patients with Idiopathic or Hereditary PAH To further elucidate the role of miR-145 in the development of PAH, miR-145 expression in lung tissue taken from patients with idiopathic PAH (iPAH) or hereditary PAH (hPAH) was compared to control lung tissue. Lung samples were obtained from patients undergoing transplantation for end stage pulmonary hypertension. Lung tissue was obtained from patients who were diagnosed with hPAH associated with mutant BMPR2 (n=5) or iPAH (n=6). Control samples (n=6) were comprised of tissue taken from lobes of lung clear of tumor from patients undergoing pneumonectomy for lung carcinoma and reported free of tumor by a pathologist.

Figure 16:
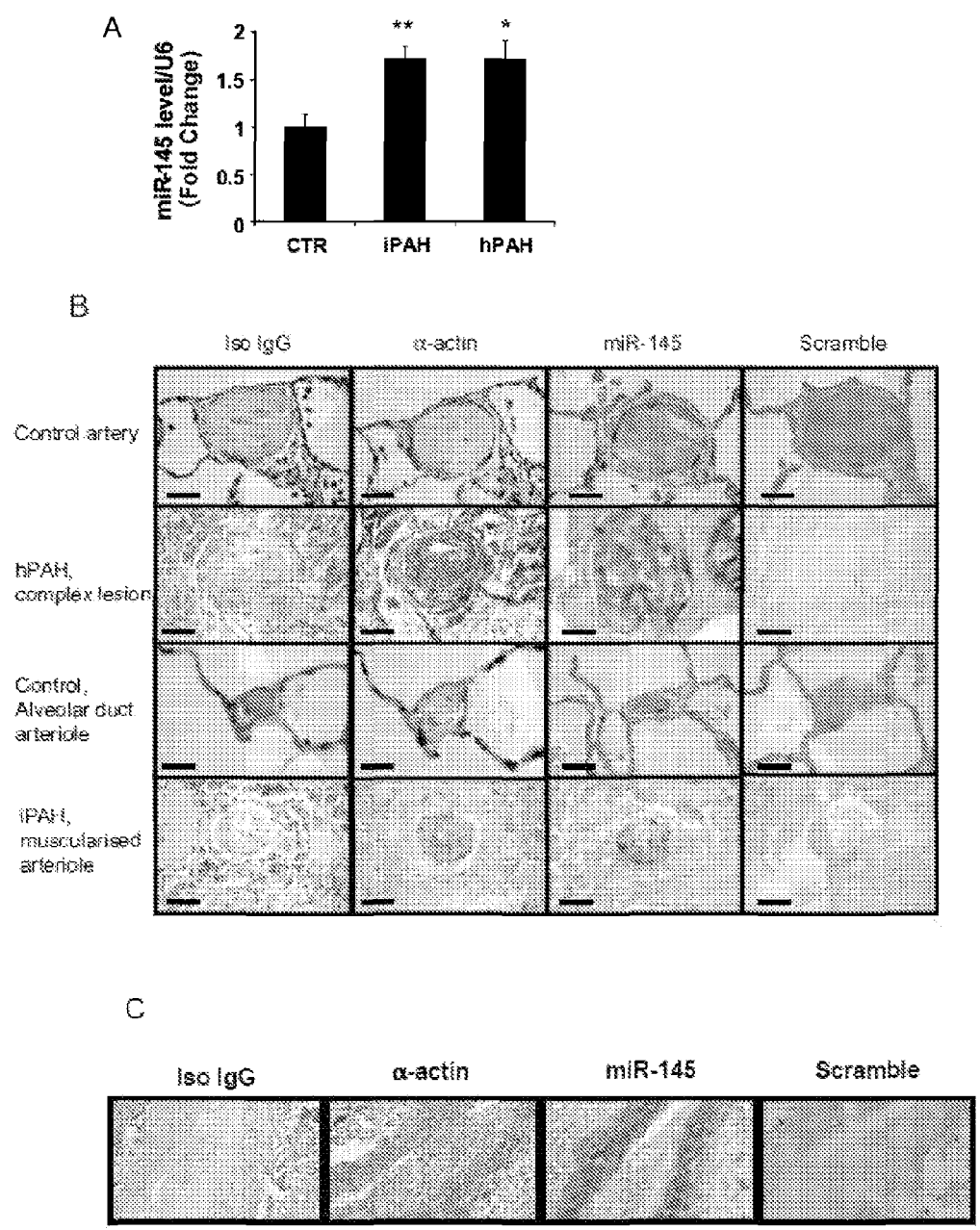
FIG. 16. Assessment of miR-145 expression level in iPAH and hPAH human lung. (A) q-PCR analysis of RNA extracted from paraffin-embedded human lungs of iPAH (n=6), hPAH (n=5) and control patients (n=6) showing the expression level of miR-145. All samples were normalized to Rnu-48 values and expressed as relative fold change, with an arbitrary value of 1 assigned to the control group. Data were analyzed using a two-way ANOVA followed by Bonferroni's post-hoc test ($*p<0.05$, $**p<0.005$). (B) In situ analysis of miR-145 expression in paraffin sections obtained from the same samples used for q-PCR analysis. A scramble probe was used as a negative control. For co-localization, α-actin was detected in the same samples using immunohistochemistry on serial sections, with nonimmune isotype-IgG antibody as a negative control. Images demonstrate increased expression of α-actin and miR-145 in a typical complex lesion and in a newly muscularised arteriole. Images all 400× magnification, scale bars=50 μm. (C) miR-145 down-regulation in the neointima lesion of hPAH patients. For co-localization, α-actin expression was detected by immunohistochemistry.

MiRNA from paraffin-embedded lung tissue was extracted and expression levels were assessed by quantitative PCR, as described above. Compared to controls, miR-145 was significantly elevated in both hPAH and iPAH samples (FIG. 16A). Next, in situ hybridization was used to localize expression of miR-145 in human lungs selected from the above patient groups (FIG. 16B). In concordance with analysis of the mouse lungs, expression of miR-145 in control lung sections was confined to smooth muscle cells in lung, including both vascular and bronchiolar lineages (FIG. 16B). PAH is characterized by the development of both concentric and plexiform arterial lesions involving the pre- and intra-acinar pulmonary arteries. In patients with iPAH and hPAH, miR-145 was expressed by arterial smooth muscle cells and observed within the muscular component of concentric lesions and plexiform vascular lesions wherever present (FIG. 16B). MiR-145 positive cells were also observed in pre- and intra-acinar arteries where vessels had become muscularized (FIG. 16B). In addition, newly muscularized arterioles at the level of alveolar ducts expressed abundant miR-145 mRNA (FIG. 16B). Although in situ localization is not quantitative, miR-145 expression was notably reduced in neointimal myofibroblasts compared to more differentiated SMCs resident within the medial layer (for example, see FIG. 16C). Taken together, in human lung, miR-145 is expressed in the smooth muscle cell compartment. MiR-145 expression is also observed within remodeled vessels of complex lesions in patients with hPAH and iPAH. In some vessels, levels of miR-145 appear reduced in neointimal cells.

Figure 17:
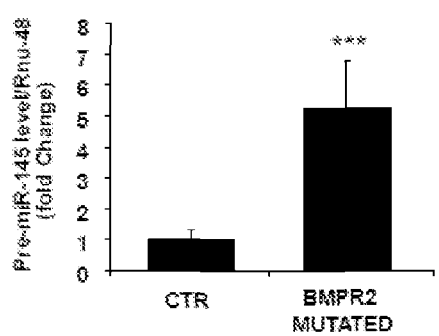
FIG. 17. Analysis of Human BMPR2-mutated PASMCs. (A) qPCR analysis of miR-145 expression in PASMCs. Total RNA was extracted from PASMCs of hPAH patients with a mutation in the BMPR2 gene. Passage 4 primary cells were used. cDNA was analyzed for pre- and mature-miR-145 expression in comparison with unaffected controls. Results were normalized to (A) Rnu-48 for the pre- and Rnu-48 for the mature miR-145 and expressed as relative fold change, with an arbitrary value of 1 assigned to the control group. Data were analyzed using an unpaired t-test ($p<0.005$, $*p<0.001$ vs control samples). (B) The same total RNA extracted from wild-type and BMPR2-mutated cells was also used for northern blot analysis in order to confirm the q-PCR result. The blot quantification was performed with Scion Image software: band intensities of the miRNA of interest were established and normalized to the relative U6 signal (C). Data were analyzed using an unpaired t-test ($***p<0.001$ vs control samples).
Figure 17:
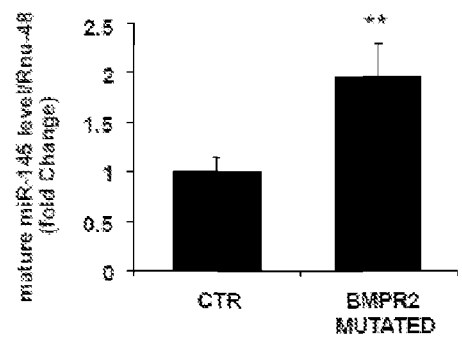
Figure 17:
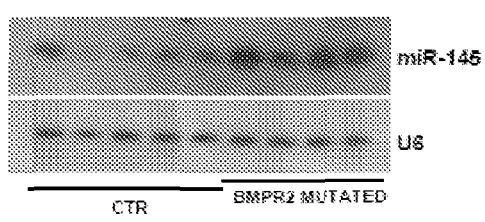
Figure 17:
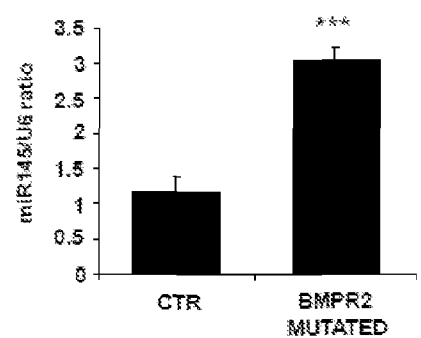

Since the growth and characteristics of PASMCs isolated from patients with BMPR2 mutations is fundamentally different to those isolated from patients without germline mutations, human primary cells in culture were used to assess the effect of BMPR2 mutations on miR-145 regulation. Primary human PASMCs obtained from PAH patients were cultured and miRNA levels at the pre-miRNA and mature miRNA level in the cultured cells were quantified. Both pre-miR-145 and mature miR-145 were significantly elevated in cells derived from patients with known BMPR2 mutations compared to unaffected controls (FIG. 17A). A northern blot analysis was performed to confirm and quantify the differential levels of the mature miR-145 in the same samples. In concordance with the PCR analysis, miR-145 was significantly elevated in RNA extracted from patients with mutations in BMPR2 compared to non-mutated control PASMCs (FIG. 17B). Therefore, basal levels of miR145 are elevated in patients with germline BMPR2 mutations.

Example 15

Effect of BMPR2 Down-Regulation on miR-143 and miR-145 Expression in Human PASMCs To evaluate in vitro the effect of an siRNA-mediated knock-down of BMPR2 on miR-143 and miR-145 expression level in human WT PASMCs, cells were transfected with a short interfering (si) sequence, able to target and down-regulate specifically BMPR2, or with a siScramble as negative control.

PASMCs were seeded in 6-well plates (1.5×105 cells/well) and grown for two days in DMEM/10% FBS. Prior to transfection, PASMCs were incubated in Optimem I for 3 h. PASMCs were transfected on Day 0 with a final concentration of 10 nM siRNA [Dharmacon™ On-TARGETplus siRNA for BMPR-II or Smad4, or siControl Nontargeting Pool (siCP) (Perbio Science UK Ltd)] in complex with DharmaFECT1™ (4 ml/well) diluted in Optimem I. The Dharmafect was incubated in half the final volume (200 ml for 1 well) of Optimem I for 5 minutes followed by addition of Optimem I (200 ml for 1 well) containing 10× final concentration of the relevant siRNA, making the siRNA at 5× final concentration. The mix was incubated for 20 minutes at room temperature to allow lipoplexes to form. The Transfection mix (400 ml/well) was dropped onto cells in fresh Optimem I (1.6 ml/well), ensuring full coverage of the well. Cells were incubated with the complexes for 4 h at 37° C., followed by replacement with DMEM/10% FBS for 24 h Day 1).

Figure 18:
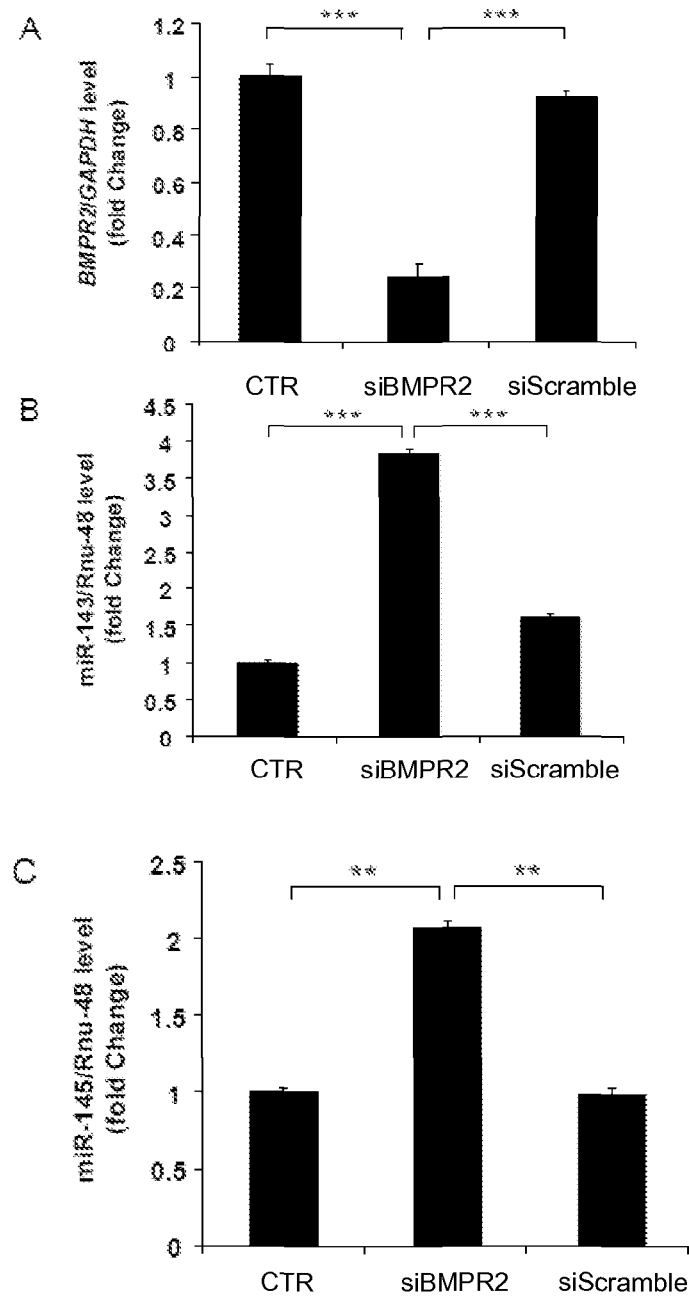
FIG. 18. miR-143 and miR-145 up-regulation in human PASMCs downregulated for BMPR2 expression via a siRNA. Primary human PASMCs were transfected with a siRNA able to target and repress specifically BMPR2 expression or with a siScramble as a negative control. Total RNA was extracted after 72 h from these samples and untreated cells for comparison. The efficiency of BMPR2 down-regulation was evaluated by (A) TaqMan Real-Time PCR. (B) miR-143 and (C) miR-145 expression were also assessed in the same samples. Results were normalized to GAPDH for BMPR2 and Rnu-48 for miR-143 and miR-145 and expressed as relative fold change, with an arbitrary value of 1 assigned to the control group. Data were analyzed using a one-way ANOVA followed by Bonferroni's post-hoc test. $p<0.005$, $*p<0.001$ cf. CTR or siScramble group as indicated.

RNA was extracted from these samples and from untreated cells after 4 days. The down-regulation of BMPR2 induced the significant up-regulation of both miR-143 and miR-145, whereas no changes were observed in untreated or siScramble-treated cells (FIG. 18).

The results of this series of experiments show the miR-145 levels are elevated in human samples from patients with hPAH and iPAH, and that miR-145 expression is localized to both medial and neointimal SMCs of complex lesions. The results also demonstrate a specific link between BMPR2 mutations and elevated levels of miR-145 in pulmonary smooth muscle cells. Interestingly, despite the up-regulation of miR-145 in the total lung of the analyzed PAH patients, the in situ localization of this miRNA in the vessels of iPAH and hPAH patients showed abundant miR-145 mRNA expression in hypertrophied arteries, pulmonary vascular lesions and newly muscularized arterioles. The manipulation of miR-145 expression appears to exert a substantial impact on the development of PAH and thus, miR-145 down-regulation is a novel therapeutic approach for PAH.

Example 16

MiR-145 Expression in BMPR2 R899X Mice

Considering the importance of miR-145 regulation in the mouse models of PAH and in PASMCs extracted from PAH patients with a mutation in the BMPR2 gene, the effect of a truncating BMPR2 mutation on miR-145 expression in heterozygous R899X+/− mice was evaluated. These mice, similar to previously described R899X transgenic mice (West et al., 2008) develop spontaneous pulmonary hypertension.

Figure 19:
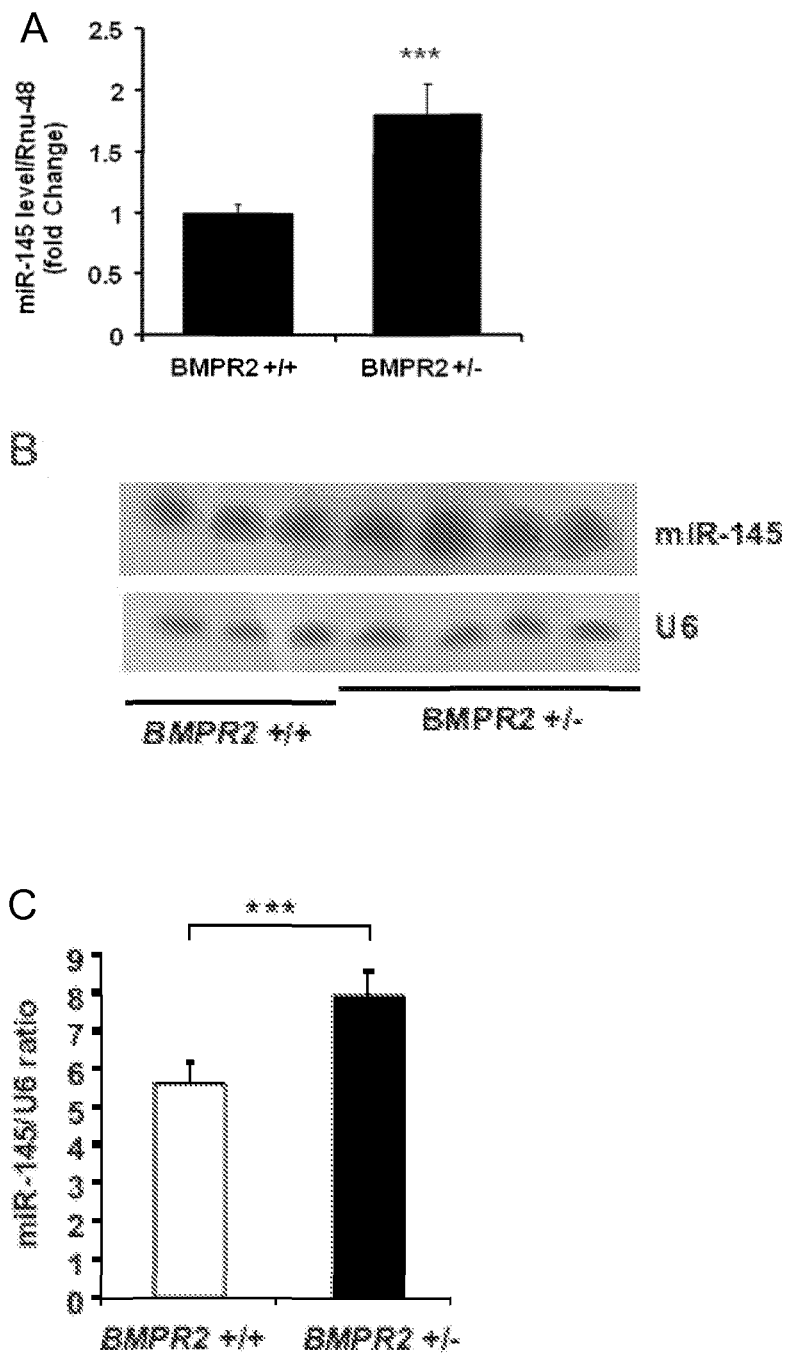
FIG. 19. miR-145 expression in wt and BMPR2 BMPR2 R899X mice. RNA was extracted from the total lung of 4 wt or BMPR2 mutated mice and assessed for miR-145 expression by (A) q-PCR, where every sample was analyzed in triplicate and results were normalized to U6 and expressed as relative fold change, with an arbitrary value of 1 assigned to the control group ($***p<0.001$ vs control samples); and (B)-(C) northern blot. (D) In situ hybridization showing miR-145 localization in the lung of the same mice. Paraffin sections were rehydrated and incubated with an anti-miR-145 or scramble probe as negative control. For colocalization, α-actin was detected in the same samples using an immunohistochemistry assay, with non-immune isotype-IgG antibody as negative control. Images ×200 magnification, scale bars=50 μm.
Figure 19:
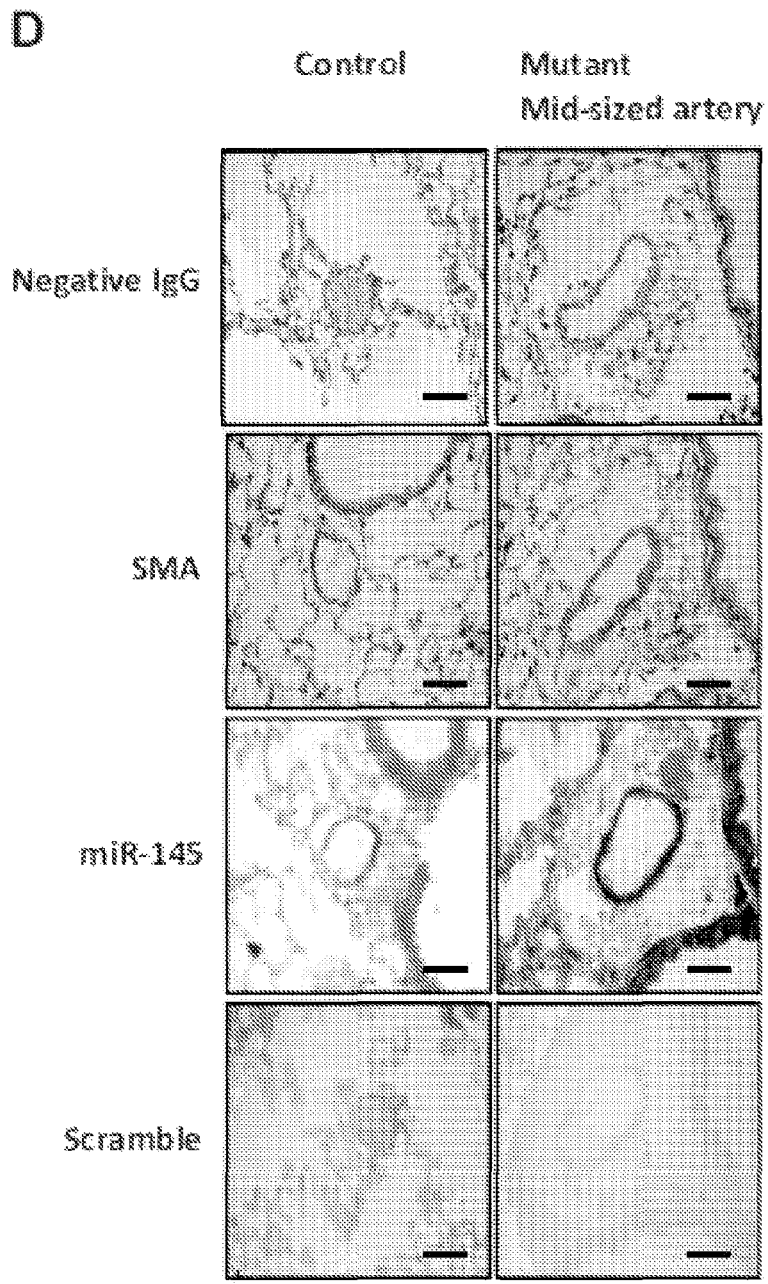

RNA was extracted from the whole lung of 6 month old mice and analyzed by q-PCR and northern blot for miR-145. This revealed a significant up-regulation of miR-145 in the mutated mice compared to controls (FIG. 19A-C). In situ localization if miR-145 in paraffin lung sections confirmed positive staining within the smooth muscle layer of pulmonary vessels and bronchi of both wt and BMPR2 mutated mice, with strong staining observed in mutated animals (FIG. 19D).

The Examples demonstrate localization of miR-145 in mouse lung to smooth muscle. Using quantitative PCR (q-PCR), increased expression of miR-145 in wildtype (wt) mice exposed to hypoxia was demonstrated. MiR-145 is significantly up-regulated in mice in response to chronic hypoxia, and genetic ablation or antimiR driven pharmacological reduction of miR-145 is protective against the development of PAH in mice.

A functional analysis of the vasculature of miR-145 −/− mice revealed a reduced pulmonary vascular response to chronic hypoxia and reduced right ventricular hypertrophy. PAH was evaluated in miR-145 knock-out and mice treated with antimiRs via measurement of systolic right ventricular pressure (sRVP), right ventricular hypertrophy (RVH) and percentage of remodeled pulmonary arteries. In addition, the percentage of remodeled vessels was significantly reduced in the knockout animals, strongly suggesting a protective role for miR-145 ablation in PAH development. The similar protective effect was observed in wt mice treated with an antimiR able to reduce miR-145 expression substantially. Thus, miR-145 deficiency and antimiR-mediated reduction resulted in significant protection from the development of PAH. In contrast, miR-143 antimiR had no effect.

Furthermore, up-regulation of miR-145 in lung tissue of patients with idiopathic and heritable PAH (iPAH, hPAH) compared to unaffected controls was observed and expression of miR-145 in SMC of remodeled vessels was demonstrated. In human tissues, pre- and mature forms of miR-145 are elevated in tissues and in isolated PASMCs obtained from PAH patients with a mutation in the BMPR2 gene as compared to controls. There were elevated levels of miR-145 expression in primary PASMCs cultured from patients with BMPR2 mutations and also in the lungs of bmpr2 deficient mice. This conserved dysregulation suggests the presence of a link between the regulation of miR-145 and the TGF-beta super-family.

MiR-145 is dysregulated in mouse models of PAH and down-regulation of miR-145 protects against the development of PAH. In patient samples of hPAH and iPAH, miR-145 is expressed in remodeled vessels and mutations in BMPR2 lead to up-regulation of miR-145 in mice and PAH patients. On the basis of these observations, there is a critical role for miR-145 in the development of PAH and manipulation of miR-145 represents a novel strategy in PAH treatment.

All publications, patents, and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

REFERENCES

1. Rich S, Dantzker D R, Ayres S M, Bergofsky E H, Brundage B H, Detre K M, Fishman A P, Goldring R M, Groves B M, Koerner S K, et al. Primary pulmonary hypertension. A national prospective study. Ann Intern Med. 1987; 107: 216-223
2. Jeffery T K, Morrell N W. Molecular and cellular basis of pulmonary vascular remodeling in pulmonary hypertension. Prog Cardiovasc Dis. 2002; 45:173-202
3. Voelkel N, Tuder R, Weir E. Pathophysiology of primary pulmonary hypertension. In: Rubin, l. Rich, s. Editors. Primary Pulmonary Hypertension, New York, N.Y.: Marcel Dekker. 1997:83-129
4. Morrell N W, Yang X, Upton P D, Jourdan K B, Morgan N, Sheares K K, Trembath R C. Altered growth responses of pulmonary artery smooth muscle cells from patients with primary pulmonary hypertension to transforming growth factor beta-(1) and bone morphogenetic proteins. Circulation. 2001; 104:790-795

5. Mandegar M, Fung Y C, Huang W, Remillard C V, Rubin L J, Yuan J X. Cellular and molecular mechanisms of pulmonary vascular remodeling: Role in the development of pulmonary hypertension. Microvasc Res. 2004; 68:75-103

6. Ambros V. The functions of animal micrornas. Nature. 2004; 431:350-355

7. Bartel D P. Micrornas: Target recognition and regulatory functions. Cell. 2009; 136:215-233

8. Guo H, Ingolia N T, Weissman J S, Bartel D P. Mammalian micrornas predominantly act to decrease target mrna levels. Nature. 2010; 466:835-840

9. Kartha R V, Subramanian S. Micrornas in cardiovascular diseases: Biology and potential clinical applications. J Cardiovasc Transl Res. 2010; 3:256-270

10. Urbich C, Kuehbacher A, Dimmeler S. Role of micrornas in vascular diseases, inflammation, and angiogenesis. Cardiovasc Res. 2008; 79:581-588

11. Cheng Y, Liu X, Yang J, Lin Y, Xu D Z, Lu Q, Deitch E A, Huo Y, Delphin E S, Zhang C. Microrna-145, a novel smooth muscle cell phenotypic marker and modulator, controls vascular neointimal lesion formation. Circ Res. 2009; 105:158-166

12. Lio A, Nakagawa Y, Hirata I, Naoe T, Akao Y. Identification of non-coding RNAs embracing microrna-143/145 cluster. Mol Cancer. 2010; 9:136

13. Xin M, Small E M, Sutherland L B, Qi X, McAnally J, Plato C F, Richardson J A, Bassel-Duby R, Olson E N. Micrornas mir-143 and mir-145 modulate cytoskeletal dynamics and responsiveness of smooth muscle cells to injury. Genes Dev. 2009; 23:2166-2178

14. Elia L, Quintavalle M, Zhang J, Contu R, Cossu L, Latronico M V, Peterson K L, Indolfi C, Catalucci D, Chen J, Courtneidge S A, Condorelli G. The knockout of mir-143 and −145 alters smooth muscle cell maintenance and vascular homeostasis in mice: Correlates with human disease. Cell Death Differ. 2009; 16:1590-1598

15. Keegan A, Morecroft I, Smillie D, Hicks M N, MacLean M R. Contribution of the 5-ht(1b) receptor to hypoxia-induced pulmonary hypertension: Converging evidence using 5-ht(1b)-receptor knockout mice and the 5-ht(1b/1d)-receptor antagonist gr127935. Circ Res. 2001; 89:1231-1239

16. Yang X, Long L, Southwood M, Rudarakanchana N, Upton P D, Jeffery T K, Atkinson C, Chen H, Trembath R C, Morrell N W. Dysfunctional smad signaling contributes to abnormal smooth muscle cell proliferation in familial pulmonary arterial hypertension. Circ Res. 2005; 96:1053-1063

17. Cikos S, Bukovska A, Koppel J. Relative quantification of mrna: Comparison of methods currently used for real-time pcr data analysis. BMC Mol Biol. 2007; 8:113 18. Livak K J, Schmittgen T D. Analysis of relative gene expression data using realtime quantitative pcr and the 2(-delta delta c(t)) method. Methods. 2001; 25:402-408

18. Cordes K R, Sheehy N T, White M P, Berry E C, Morton S U, Muth A N, Lee T H, Miano J M, Ivey K N, Srivastava D. Mir-145 and mir-143 regulate smooth muscle cell fate and plasticity. Nature. 2009; 460:705-710

19. Davis B N, Hilyard A C, Lagna G, Hata A. Smad proteins control drosha-mediated microrna maturation. Nature. 2008; 454:56-61

20. Courboulin A, Paulin R, Giguère N J, Saksouk N, Perreault T, Meloche J, Paquet E R, Biardel S, Provencher S, Côté J, Simard M J, Bonnet S. Role for mir-204 in human pulmonary arterial hypertension. The Journal of Experimental Medicine. 2011; 208:535-548

21. Davis-Dusenbery B N, Chan M C, Reno K E, Weisman A S, Layne M D, Lagna G, Hata A. Downregulation of klf4 by mir-143/145 is critical for modulation of vascular smooth muscle cell phenotype by tgf-{beta} and bmp. J Biol Chem. 2011; 286:28097-110

22. Long X, Miano J M. Tgf{beta} 1 utilizes distinct pathways for the transcriptional activation of microrna 143/145 in human coronary artery smooth muscle cells. J Biol Chem. 2011; 286, 30119-30129

23. Boettger T, Beetz N, Kostin S, Schneider J, Kruger M, Hein L, Braun T. Acquisition of the contractile phenotype by murine arterial smooth muscle cells depends on the mir143/145 gene cluster. J Clin Invest. 2009; 119:2634-2647

24. Kano M, Seki N, Kikkawa N, Fujimura L, Hoshino I, Akutsu Y, Chiyomaru T, Enokida H, Nakagawa M, Matsubara H. Mir-145, mir-133a and mir-133b: Tumorsuppressive mirnas target fscn1 in esophageal squamous cell carcinoma. Int J Cancer. 2010; 127:2804-2814

25. Xu N, Papagiannakopoulos T, Pan G, Thomson J A, Kosik K S. Microrna-145 regulates oct4, sox2, and klf4 and represses pluripotency in human embryonic stem cells. Cell. 2009; 137:647-658

26. West J, Harral J, Lane K, Deng Y, Ickes B, Crona D, Albu 5, Stewart D, Fagan K. Mice expressing bmpr2r899x transgene in smooth muscle develop pulmonary vascular lesions. Am. J Physiol Lung Cell Mol Physiol. 2008; 295: L744-755

27. Leyns L, Bouwmeester T, Kim S H, Piccolo S, De Robertis E M. Frzb-1 is a secreted antagonist of wnt signaling expressed in the spemann organizer. Cell. 1997; 88:747-756

28. Hsieh J C, Kodjabachian L, Rebbert M L, Rattner A, Smallwood P M, Samos C H, Nusse R, Dawid. I B, Nathans J. A new secreted protein that binds to wnt proteins and inhibits their activities. Nature. 1999; 398:431-436

29. Jiang Y, Luo W, Howe P H. Dab2 stabilizes axin and attenuates wnt/beta-catenin signaling by preventing protein phosphatase 1 (pp1)-axin interactions. Oncogene. 2009; 28:2999-3007

30. Baldin V, Lukas J, Marcote M J, Pagano M, Draetta G. Cyclin dl is a nuclear protein required for cell cycle progression in g1. Genes Dev. 1993; 7:812-821

31. Baranwal S, Alahari S K. Molecular mechanisms controlling e-cadherin expression in breast cancer. Biochem Biophys Res Commun. 2009; 384:6-11

The invention claimed is:

1. A method of treating or preventing pulmonary arterial hypertension (PAH) in a subject in need thereof comprising administering to the subject an effective dose of an inhibitor of miR-145, wherein the PAH is treated or prevented in the subject.

2. The method of claim 1, wherein the inhibitor of miR-145 is an antisense oligonucleotide comprising a sequence that is at least partially complementary to a mature miR-145 sequence.

3. The method of claim 2, wherein the antisense oligonucleotide comprises a sequence that is at least partially complementary to a sequence of 5'-GUCCAGUUUUC-CCAGGAAUCCCU-3' (SEQ ID NO: 1) or 5'-GGAUUC-CUGGAAAUACUGUUCU-3' (SEQ ID NO: 2).

4. The method of claim 2, wherein the antisense oligonucleotide comprises at least one sugar modification.

5. The method of claim 4, wherein the at least one sugar modification is a 2'-O-alkyl modification or a bicyclic sugar nucleoside modification.

6. The method of claim 5, wherein the bicyclic sugar nucleoside modification is a locked nucleic acid.

7. The method of claim 2, wherein the antisense oligonucleotide comprises at least one backbone modification.

8. The method of claim 7, wherein the backbone modification is a phosphorothioate linkage.

9. The method of claim 2, wherein the antisense oligonucleotide is about 8 to about 18 nucleotides in length.

10. The method of claim 9, wherein the antisense oligonucleotide is about 12 to about 16 nucleotides in length.

11. The method of claim 1, wherein the inhibitor is administered the subject by an inhalational route of administration.

12. The method of claim 11, wherein the inhibitor is formulated as a dry powder.

13. The method of claim 11, wherein the inhibitor is formulated as a liquid aerosol.

14. The method of claim 1, wherein the subject is a human.

15. The method of claim 14, wherein the human has a mutation in the gene encoding the bone morphogenetic protein type-2 receptor.

16. A kit for the treatment or prevention of pulmonary arterial hypertension (PAH) comprising an effective dose of an inhibitor of miR-145 for treating or preventing PAH and an administration device.

17. The kit of claim 16, wherein the administration device is an inhaler.

18. The kit of claim 16, wherein the inhibitor of miR-145 is an antisense oligonucleotide comprising a sequence that is at least partially complementary to a mature milk-145 sequence.

19. The kit of claim 18, wherein the antisense oligonucleotide comprises a sequence that is at least partially complementary to a sequence of 5'-GUCCAGUUUUCCCAG-GAAUCCCU-3' (SEQ ID NO: 1) or 5'-GGAUUCCUGGAAAUACUGUUCU-3' (SEQ ID NO: 2).

20. The kit of claim 16, wherein the inhibitor is formulated as a powder or liquid aerosol contained within the administration device.

* * * * *

SEQUENCE LISTING

<160> NUMBER OF SEQ ID NOS: 16

<210> SEQ ID NO 1
<211> LENGTH: 23
<212> TYPE: RNA

```
<213> ORGANISM: Homo sapiens

<400> SEQUENCE: 1
guccaguuuu cccaggaauc ccu                                         23

<210> SEQ ID NO 2
<211> LENGTH: 22
<212> TYPE: RNA
<213> ORGANISM: Homo sapiens

<400> SEQUENCE: 2
ggauuccugg aaauacuguu cu                                          22

<210> SEQ ID NO 3
<211> LENGTH: 88
<212> TYPE: RNA
<213> ORGANISM: Homo sapiens

<400> SEQUENCE: 3
caccuugucc ucacggucca guuucccag gaaucccuua gaugcuaaga ugggauucc   60 uggaaauacu guucuugagg ucaugguu                                    88

<210> SEQ ID NO 4
<211> LENGTH: 23
<212> TYPE: RNA
<213> ORGANISM: Mus sp.

<400> SEQUENCE: 4
guccaguuuu cccaggaauc ccu                                         23

<210> SEQ ID NO 5
<211> LENGTH: 22
<212> TYPE: RNA
<213> ORGANISM: Mus sp.

<400> SEQUENCE: 5
auuccuggaa auacuguucu ug                                          22

<210> SEQ ID NO 6
<211> LENGTH: 70
<212> TYPE: RNA
<213> ORGANISM: Mus sp.

<400> SEQUENCE: 6
cucacgaucc aguuucccca ggaaucccuu ggaugcuaag auggggauuc cuggaaauac 60
uguucuugag                                                        70

<210> SEQ ID NO 7
<211> LENGTH: 23
<212> TYPE: RNA
<213> ORGANISM: Artificial Sequence
<220> FEATURE:
<223> OTHER INFORMATION: miR-145 antisense oligonucleotide

<400> SEQUENCE: 7
agggauuccu gggaaaacug gac                                         23

<210> SEQ ID NO 8
<211> LENGTH: 16
<212> TYPE: RNA
<213> ORGANISM: Artificial Sequence
<220> FEATURE:
<223> OTHER INFORMATION: miR-145 antisense oligonucleotide
```

<400> SEQUENCE: 8
ccugggaaaa cuggac                                                      16

<210> SEQ ID NO 9
<211> LENGTH: 14
<212> TYPE: RNA
<213> ORGANISM: Artificial Sequence
<220> FEATURE:
<223> OTHER INFORMATION: miR-145 antisense oligonucleotide

<400> SEQUENCE: 9
ugggaaaacu ggac                                                        14

<210> SEQ ID NO 10
<211> LENGTH: 12
<212> TYPE: RNA
<213> ORGANISM: Artificial Sequence
<220> FEATURE:
<223> OTHER INFORMATION: miR-145 antisense oligonucleotide

<400> SEQUENCE: 10
ggaaaacugg ac                                                          12

<210> SEQ ID NO 11
<211> LENGTH: 10
<212> TYPE: RNA
<213> ORGANISM: Artificial Sequence
<220> FEATURE:
<223> OTHER INFORMATION: miR-145 antisense oligonucleotide

<400> SEQUENCE: 11
aaaacuggac                                                             10

<210> SEQ ID NO 12
<211> LENGTH: 8
<212> TYPE: RNA
<213> ORGANISM: Artificial Sequence
<220> FEATURE:
<223> OTHER INFORMATION: miR-145 antisense oligonucleotide

<400> SEQUENCE: 12 aacuggac                                                                8

<210> SEQ ID NO 13
<211> LENGTH: 16
<212> TYPE: RNA
<213> ORGANISM: Artificial Sequence
<220> FEATURE:
<223> OTHER INFORMATION: miR-145 antisense oligonucleotide
<220> FEATURE:
<221> NAME/KEY: misc_feature
<222> LOCATION: (1)..(16)
<223> OTHER INFORMATION: May be fully phosphorothiolated
<220> FEATURE:
<221> NAME/KEY: misc_feature
<222> LOCATION: (1)..(16)
<223> OTHER INFORMATION: May be composed of locked nucleic acids
<220> FEATURE:
<221> NAME/KEY: misc_feature
<222> LOCATION: (1)..(16)
<223> OTHER INFORMATION: May be composed of a mixture of locked nucleic
      acids and deoxyribonucleic acids

<400> SEQUENCE: 13
uccugggaaa acugga                                                      16

```
<210> SEQ ID NO 14
<211> LENGTH: 16
<212> TYPE: DNA
<213> ORGANISM: Homo sapiens

<400> SEQUENCE: 14
tacagtgctt catctc                                                     16

<210> SEQ ID NO 15
<211> LENGTH: 22
<212> TYPE: RNA
<213> ORGANISM: Homo sapiens

<400> SEQUENCE: 15
uucccuuugu cauccaugc cu                                               22

<210> SEQ ID NO 16
<211> LENGTH: 21
<212> TYPE: RNA
<213> ORGANISM: Homo sapiens

<400> SEQUENCE: 16
gcugggaagg caaagggacg u                                               21
```